United States Patent
Anand et al.

(10) Patent No.: US 10,531,882 B2
(45) Date of Patent: Jan. 14, 2020

(54) METHODS AND DEVICES FOR TREATING STROKE

(71) Applicant: Alcyone Lifesciences, Inc., Lowell, MA (US)

(72) Inventors: P J Anand, Lowell, MA (US); John Ekholm, Seattle, WA (US); Deep Arjun Singh, Cambridge, MA (US)

(73) Assignee: Alcyone Lifesciences, Inc., Lowell, MA (US)

( * ) Notice: Subject to any disclaimer, the term of this patent is extended or adjusted under 35 U.S.C. 154(b) by 18 days.

(21) Appl. No.: 15/397,947

(22) Filed: Jan. 4, 2017

(65) Prior Publication Data

US 2017/0189040 A1    Jul. 6, 2017

Related U.S. Application Data

(60) Provisional application No. 62/274,582, filed on Jan. 4, 2016.

(51) Int. Cl.
*A61B 17/22*   (2006.01)
*A61M 1/00*    (2006.01)

(52) U.S. Cl.
CPC ............ *A61B 17/22* (2013.01); *A61M 1/008* (2013.01); *A61M 1/0058* (2013.01); *A61B 2017/22079* (2013.01); *A61B 2017/22088* (2013.01)

(58) Field of Classification Search
CPC ................ A61M 1/0058; A61M 1/008; A61M 25/0102; A61M 2025/0008;
(Continued)

(56) References Cited

U.S. PATENT DOCUMENTS

| 2,830,587 A | 4/1958 | Everett |
| 3,460,537 A | 8/1969 | Zeis |

(Continued)

FOREIGN PATENT DOCUMENTS

| CN | 101123919 A | 2/2008 |
| CN | 101657189 A | 2/2010 |

(Continued)

OTHER PUBLICATIONS

Sampson et al., Progress report of a Phase I study of the intracerebral microinfusion of a recombinant chimeric protein composed of transforming growth factor (tgf)-a and a mutated form of the Pseudomonas exotoxin termed PE-38 (TP-38) for the treatment of malignant brain tumors, (2003), (continued below in Box V).*

(Continued)

*Primary Examiner* — Theodore J Stigell
(74) *Attorney, Agent, or Firm* — Nutter McClennen & Fish LLP

(57) ABSTRACT

Methods and devices are disclosed herein that allow for infusion and aspiration through a single device. The device can be used to treat a stroke by delivering the device to the site of a blood clot and simultaneously or sequentially infusing a thrombolytic or other drug into the clot and aspirating the dissolving clot from the patient. The methods and devices can advantageously permit more efficient thrombolytic infusion and clot aspiration. Modular systems are also disclosed, as are methods of treating subdural hematoma or other conditions.

18 Claims, 21 Drawing Sheets

(58) Field of Classification Search
CPC ........... A61M 2210/0693; A61B 17/22; A61B 2017/22079; A61B 2017/22088; A61B 90/10; A61B 2017/22084; A61B 2217/005; A61B 2217/007; A61B 2017/22082

See application file for complete search history.

(56) References Cited

U.S. PATENT DOCUMENTS

| | | | |
|---|---|---|---|
| 3,886,948 | A | 6/1975 | Hakim |
| 4,146,029 | A | 3/1979 | Ellinwood, Jr. |
| 4,692,146 | A | 9/1987 | Hilger |
| 4,885,945 | A | 12/1989 | Chiodo |
| 4,917,686 | A | 4/1990 | Bayston et al. |
| 4,979,284 | A | 12/1990 | McMurtry et al. |
| 5,059,178 | A * | 10/1991 | Ya .................... A61B 17/22 604/101.03 |
| 5,088,208 | A | 2/1992 | Wells et al. |
| 5,101,548 | A | 4/1992 | McMurtry et al. |
| 5,190,046 | A | 3/1993 | Shturman |
| 5,407,431 | A | 4/1995 | Botich et al. |
| 5,415,648 | A | 5/1995 | Malay et al. |
| 5,419,761 | A * | 5/1995 | Narayanan ....... A61B 17/22012 604/22 |
| 5,484,412 | A * | 1/1996 | Pierpont ............. A61M 25/104 604/101.03 |
| 5,509,910 | A | 4/1996 | Lunn |
| 5,590,657 | A | 1/1997 | Cain et al. |
| 5,620,479 | A | 4/1997 | Diederich |
| 5,624,396 | A | 4/1997 | McNamara et al. |
| 5,695,518 | A | 12/1997 | Laerum |
| 5,720,720 | A | 2/1998 | Laske et al. |
| 5,782,645 | A | 7/1998 | Stobie et al. |
| 5,843,150 | A | 12/1998 | Dreessen et al. |
| 5,868,711 | A | 2/1999 | Kramer et al. |
| 5,954,687 | A | 9/1999 | Baudino |
| 5,963,367 | A | 10/1999 | Aksyuk et al. |
| 6,061,587 | A | 5/2000 | Kucharczyk et al. |
| 6,176,842 | B1 | 1/2001 | Tachibana et al. |
| 6,193,963 | B1 | 2/2001 | Stern et al. |
| 6,200,291 | B1 | 3/2001 | Di Pietro |
| 6,224,566 | B1 | 5/2001 | Loeb |
| 6,309,634 | B1 | 10/2001 | Bankiewicz et al. |
| 6,454,945 | B1 | 9/2002 | Weigl et al. |
| 6,464,662 | B1 | 10/2002 | Raghavan et al. |
| 6,464,687 | B1 | 10/2002 | Ishikawa et al. |
| 6,471,993 | B1 | 10/2002 | Shastri et al. |
| 6,547,779 | B2 | 4/2003 | Levine et al. |
| 6,599,274 | B1 | 7/2003 | Kucharczyk et al. |
| 6,610,235 | B1 | 8/2003 | Lebouitz et al. |
| 6,626,902 | B1 | 9/2003 | Kucharczyk et al. |
| 6,706,009 | B2 | 3/2004 | Diermann et al. |
| 6,803,568 | B2 | 10/2004 | Bousse et al. |
| 6,953,575 | B2 | 10/2005 | Bankiewicz et al. |
| 6,958,059 | B2 * | 10/2005 | Zadno-Azizi .... A61B 17/12109 604/103.01 |
| 7,029,697 | B2 | 4/2006 | Segura et al. |
| 7,048,716 | B1 | 5/2006 | Kucharczyk et al. |
| 7,220,269 | B1 * | 5/2007 | Ansel ............... A61B 17/22031 604/22 |
| 7,316,676 | B2 | 1/2008 | Peyman et al. |
| 7,494,486 | B2 * | 2/2009 | Mische ............ A61B 17/22012 604/509 |
| 7,534,613 | B2 | 5/2009 | Bankiewicz et al. |
| 7,549,989 | B2 | 6/2009 | Morgan et al. |
| 7,588,574 | B2 | 9/2009 | Assell et al. |
| 7,662,143 | B2 * | 2/2010 | Carrison ............ A61M 25/1011 604/509 |
| 7,690,325 | B2 | 4/2010 | Henderson et al. |
| 7,713,269 | B2 | 5/2010 | Auge, II et al. |
| 7,771,387 | B2 | 8/2010 | Porter |
| 7,842,006 | B2 | 11/2010 | Wang et al. |
| 7,984,929 | B2 | 7/2011 | Gill |
| 8,128,600 | B2 | 3/2012 | Gill |
| 8,192,366 | B2 | 6/2012 | Mauge et al. |
| 8,231,600 | B2 * | 7/2012 | von Hoffmann ...... A61B 17/22 604/508 |
| 8,282,566 | B2 | 10/2012 | Mauge et al. |
| 8,309,355 | B2 | 11/2012 | Bankiewicz et al. |
| 8,347,696 | B2 | 1/2013 | Espinosa et al. |
| 8,444,665 | B2 * | 5/2013 | Tsugita ............ A61B 17/12136 606/200 |
| 8,539,905 | B2 | 9/2013 | Cady et al. |
| 8,602,644 | B2 | 12/2013 | Choi |
| 8,790,317 | B2 | 7/2014 | Olbricht et al. |
| 8,814,853 | B2 | 8/2014 | Bosel |
| 8,992,458 | B2 | 3/2015 | Singh et al. |
| 9,255,245 | B2 | 2/2016 | Bernick et al. |
| 9,445,838 | B2 | 9/2016 | Wei et al. |
| 9,844,585 | B2 | 12/2017 | Olbricht et al. |
| 9,919,129 | B2 | 3/2018 | Singh et al. |
| 10,065,016 | B2 | 9/2018 | Singh et al. |
| 2001/0005552 | A1 | 6/2001 | Berg et al. |
| 2002/0055702 | A1 | 5/2002 | Atala et al. |
| 2002/0055731 | A1 | 5/2002 | Atala et al. |
| 2002/0091407 | A1 * | 7/2002 | Zadno-Azizi .......... A61B 17/22 606/200 |
| 2002/0099356 | A1 | 7/2002 | Unger et al. |
| 2002/0138036 | A1 | 9/2002 | Babaev |
| 2002/0193817 | A1 | 12/2002 | Lal et al. |
| 2003/0009153 | A1 | 1/2003 | Brisken et al. |
| 2003/0048969 | A1 | 3/2003 | Hunter et al. |
| 2003/0093032 | A1 | 5/2003 | Py et al. |
| 2003/0138403 | A1 | 7/2003 | Drustrup |
| 2003/0148539 | A1 | 8/2003 | van Dam et al. |
| 2003/0205947 | A1 | 11/2003 | Klee et al. |
| 2003/0216685 | A1 | 11/2003 | Porter |
| 2003/0216714 | A1 | 11/2003 | Gill |
| 2004/0073114 | A1 | 4/2004 | Oliver et al. |
| 2004/0106904 | A1 | 6/2004 | Gonnelli et al. |
| 2004/0176732 | A1 | 9/2004 | Frazier et al. |
| 2004/0186384 | A1 | 9/2004 | Babaev |
| 2004/0220543 | A1 | 11/2004 | Heruth et al. |
| 2004/0260241 | A1 | 12/2004 | Yamamoto et al. |
| 2005/0035983 | A1 | 2/2005 | Cruchon-Dupeyrat et al. |
| 2005/0125007 | A1 | 6/2005 | Gill |
| 2005/0137134 | A1 | 6/2005 | Gill et al. |
| 2005/0137531 | A1 | 6/2005 | Prausnitz et al. |
| 2005/0143790 | A1 | 6/2005 | Kipke et al. |
| 2005/0154297 | A1 | 7/2005 | Gill |
| 2005/0177117 | A1 | 8/2005 | Crocker et al. |
| 2005/0190999 | A1 | 9/2005 | Hunter et al. |
| 2005/0236566 | A1 | 10/2005 | Liu |
| 2005/0269251 | A1 | 12/2005 | Cork et al. |
| 2005/0277862 | A1 | 12/2005 | Anand |
| 2006/0003310 | A1 | 1/2006 | Klauke et al. |
| 2006/0025752 | A1 | 2/2006 | Broaddus et al. |
| 2006/0122677 | A1 | 6/2006 | Vardiman |
| 2006/0135945 | A1 | 6/2006 | Bankiewicz et al. |
| 2006/0211944 | A1 | 9/2006 | Mauge et al. |
| 2006/0211945 | A1 | 9/2006 | Mauge et al. |
| 2006/0211946 | A1 | 9/2006 | Mauge et al. |
| 2007/0005017 | A1 | 1/2007 | Alchas et al. |
| 2007/0016041 | A1 | 1/2007 | Nita |
| 2007/0055180 | A1 | 3/2007 | Deem et al. |
| 2007/0088295 | A1 | 4/2007 | Bankiewicz |
| 2007/0123843 | A1 | 5/2007 | Gill |
| 2007/0128083 | A1 | 6/2007 | Yantz et al. |
| 2007/0163137 | A1 | 7/2007 | Hunter et al. |
| 2007/0191767 | A1 | 8/2007 | Hennessy et al. |
| 2007/0250054 | A1 | 10/2007 | Drake |
| 2007/0276340 | A1 | 11/2007 | Poston et al. |
| 2008/0004572 | A1 | 1/2008 | Morris et al. |
| 2008/0091104 | A1 | 4/2008 | Abraham |
| 2008/0275466 | A1 | 11/2008 | Skakoon |
| 2008/0294096 | A1 | 11/2008 | Uber, III et al. |
| 2008/0302960 | A1 | 12/2008 | Meister et al. |
| 2009/0030373 | A1 | 1/2009 | Gill |
| 2009/0048508 | A1 | 2/2009 | Gill et al. |
| 2009/0071833 | A1 | 3/2009 | Gorfinkel et al. |
| 2009/0088730 | A1 | 4/2009 | Hoofnagle et al. |
| 2009/0112278 | A1 | 4/2009 | Wingeier et al. |
| 2009/0124976 | A1 | 5/2009 | Mittermeyer |

(56) References Cited

U.S. PATENT DOCUMENTS

| | | |
|---|---|---|
| 2009/0143659 A1 | 6/2009 | Li et al. |
| 2009/0143764 A1 | 6/2009 | Nelson |
| 2009/0198218 A1 | 8/2009 | Gill et al. |
| 2009/0224529 A1 | 9/2009 | Gill |
| 2009/0270790 A1 | 10/2009 | Raghavan |
| 2009/0279815 A1 | 11/2009 | Hunter et al. |
| 2009/0304314 A1 | 12/2009 | Derrick et al. |
| 2010/0030102 A1 | 2/2010 | Poston et al. |
| 2010/0030148 A1 | 2/2010 | Alchas et al. |
| 2010/0042070 A1 | 2/2010 | Gill et al. |
| 2010/0042098 A1 | 2/2010 | Cross et al. |
| 2010/0098767 A1 | 4/2010 | Olbricht et al. |
| 2010/0121307 A1 | 5/2010 | Lockard et al. |
| 2010/0130884 A1 | 5/2010 | Linninger |
| 2010/0131000 A1 | 5/2010 | DeMello et al. |
| 2010/0145304 A1 | 6/2010 | Cressman |
| 2010/0160851 A1* | 6/2010 | Dimalanta .......... A61F 9/00736 604/22 |
| 2010/0168583 A1 | 7/2010 | Dausch et al. |
| 2010/0185179 A1 | 7/2010 | Chan |
| 2010/0199788 A1 | 8/2010 | Ayliffe et al. |
| 2010/0217196 A1 | 8/2010 | Nelson |
| 2010/0217228 A1 | 8/2010 | Grahn et al. |
| 2010/0217236 A1 | 8/2010 | Gill et al. |
| 2010/0256549 A1 | 10/2010 | Kralick et al. |
| 2010/0298163 A1 | 11/2010 | Juncker et al. |
| 2010/0312193 A1 | 12/2010 | Stratton et al. |
| 2010/0318061 A1 | 12/2010 | Derrick et al. |
| 2010/0318064 A1 | 12/2010 | Derrick et al. |
| 2010/0324127 A1 | 12/2010 | Kay |
| 2011/0003330 A1 | 1/2011 | Durack |
| 2011/0009879 A1 | 1/2011 | Derrick et al. |
| 2011/0098580 A1 | 4/2011 | Mikhail et al. |
| 2011/0106054 A1 | 5/2011 | Osborne et al. |
| 2011/0137289 A1 | 6/2011 | Kunst |
| 2011/0178505 A1 | 7/2011 | Odland et al. |
| 2011/0184503 A1 | 7/2011 | Xu et al. |
| 2011/0200244 A1 | 8/2011 | Ashton et al. |
| 2011/0218494 A1 | 9/2011 | Gerrans et al. |
| 2011/0275994 A1 | 11/2011 | Iwase et al. |
| 2011/0282319 A1 | 11/2011 | Gill |
| 2011/0301235 A1 | 12/2011 | Erlanson et al. |
| 2012/0019270 A1 | 1/2012 | Amodei et al. |
| 2012/0041394 A1 | 2/2012 | Haider |
| 2012/0046666 A1 | 2/2012 | Klein |
| 2012/0060847 A1 | 3/2012 | Stratton et al. |
| 2012/0065496 A1 | 3/2012 | Stratton et al. |
| 2012/0083739 A1 | 4/2012 | Nelson |
| 2012/0083742 A1 | 4/2012 | Nelson |
| 2012/0123391 A1 | 5/2012 | Gill et al. |
| 2012/0209110 A1 | 8/2012 | Bankiewicz et al. |
| 2012/0209303 A1 | 8/2012 | Frankhouser et al. |
| 2012/0257846 A1 | 10/2012 | Derrick et al. |
| 2012/0302959 A1 | 11/2012 | Fielder et al. |
| 2012/0310182 A1 | 12/2012 | Fielder et al. |
| 2012/0310215 A1 | 12/2012 | Stout et al. |
| 2013/0019488 A1 | 1/2013 | McMurtry et al. |
| 2013/0035560 A1 | 2/2013 | Anand et al. |
| 2013/0035574 A1 | 2/2013 | Anand |
| 2013/0035660 A1 | 2/2013 | Anand |
| 2013/0046230 A1 | 2/2013 | Lewis, Jr. et al. |
| 2013/0072882 A1 | 3/2013 | Ogawa et al. |
| 2013/0079596 A1 | 3/2013 | Smith |
| 2013/0079779 A1 | 3/2013 | Smith |
| 2013/0204202 A1 | 8/2013 | Trombly et al. |
| 2013/0310767 A1 | 11/2013 | Solar et al. |
| 2014/0039459 A1 | 2/2014 | Folk et al. |
| 2014/0171760 A1 | 6/2014 | Singh et al. |
| 2014/0171902 A1 | 6/2014 | Singh et al. |
| 2014/0276417 A1 | 9/2014 | Nelson |
| 2014/0324080 A1 | 10/2014 | Wallace |
| 2014/0371711 A1 | 12/2014 | Singh et al. |
| 2014/0371712 A1 | 12/2014 | Olbricht et al. |
| 2015/0038949 A1 | 2/2015 | Singh et al. |
| 2015/0133887 A1 | 5/2015 | Singh et al. |
| 2015/0141914 A1 | 5/2015 | Fasano et al. |
| 2015/0328435 A1 | 11/2015 | Mathis et al. |
| 2016/0213312 A1 | 7/2016 | Singh et al. |
| 2016/0346505 A1 | 12/2016 | Gill et al. |
| 2017/0071624 A1* | 3/2017 | McGuckin, Jr. .... A61M 1/0058 |
| 2017/0258996 A1 | 9/2017 | Anand et al. |
| 2018/0193595 A1 | 7/2018 | Singh et al. |
| 2019/0009055 A1 | 1/2019 | Singh et al. |
| 2019/0117886 A1 | 4/2019 | Anand |
| 2019/0142453 A1* | 5/2019 | Efremkin ........... A61B 17/2202 606/7 |

FOREIGN PATENT DOCUMENTS

| | | |
|---|---|---|
| EP | 2 042 212 A1 | 4/2009 |
| JP | 2009-507531 A | 2/2009 |
| JP | 2009-526589 A | 7/2009 |
| JP | 2010-501233 A | 1/2010 |
| JP | 2011-212502 A | 10/2011 |
| WO | 95/05864 A1 | 3/1995 |
| WO | 97/00442 A1 | 1/1997 |
| WO | 97/17105 A1 | 5/1997 |
| WO | 97/40874 A1 | 11/1997 |
| WO | 97/48425 A2 | 12/1997 |
| WO | 98/52064 A1 | 11/1998 |
| WO | 99/52585 A1 | 10/1999 |
| WO | 00/51669 A1 | 9/2000 |
| WO | 02/068036 A1 | 9/2002 |
| WO | 02/085431 A2 | 10/2002 |
| WO | 2004/060465 A2 | 7/2004 |
| WO | 2006/015091 A2 | 2/2006 |
| WO | 2007/093778 A1 | 8/2007 |
| WO | 2007/104953 A1 | 9/2007 |
| WO | 2007/133545 A2 | 11/2007 |
| WO | 2008/100930 A2 | 8/2008 |
| WO | 2008/134509 A1 | 11/2008 |
| WO | 2010/006293 A2 | 1/2010 |
| WO | 2010/081072 A2 | 7/2010 |
| WO | 2011/098769 A1 | 8/2011 |
| WO | 2011/109735 A2 | 9/2011 |
| WO | 2012/145652 A1 | 10/2012 |
| WO | 2013/019830 A2 | 2/2013 |
| WO | 2013/119662 A1 | 8/2013 |
| WO | 2014/016591 A1 | 1/2014 |

OTHER PUBLICATIONS

Journal of Neuro-Oncology 65:27-35.*

Burmeister et al.; Improved Ceramic-Based Multisite Microelectrode for Rapid Measurements of L-Glutamate in the CNS; Journal of Neuroscience Methods 119 (2002) 163-171; Elsevier Science B.V.

Chinese Office Action for Application No. 201280046268.8, dated May 27, 2015 (45 pages).

Debinski, W., et al., "Convection-enhanced Delivery for the Treatment of Brain Tumors," Expert Rev Neurother. Oct. 2009; 9(10): 1519-1527.

Extended European Search Report for Application No. 12819276.2, dated Mar. 23, 2015 (7 pages).

Extended European Search Report for Application No. 13865917.2, dated Aug. 17, 2016 (6 pages).

Extended European Search Report for Application No. 14814380.3, dated Nov. 11, 2016. (7 pages).

Extended European Search Report for Application No. 14831460.2, dated Mar. 2, 2017 (7 pages).

Fiandaca, M., et al., "Use of Convection-Enhanced Delivery with Liposomal Toxins in Neurooncology," Toxins 2011, 3 (4), 369-397.

International Search Report for International Application No. PCT/US2011/027238, dated Nov. 16, 2011.

International Search Report and Written Opinion for Application No. PCT/US2012/049100, dated Jan. 29, 2013. (12 pages).

International Search Report and Written Opinion for Application No. PCT/US2013/076084 dated Mar. 11, 2014 (13 Pages).

International Search Report and Written Opinion for Application No. PCT/US2014/042726 dated Oct. 28, 2014 (13 Pages).

Invitation to Pay Additonal Fees for Application No. PCT/US2014/049031, dated Nov. 24, 2014 (2 pages).

(56) References Cited

OTHER PUBLICATIONS

International Search Report and Written Opinion for Application No. PCT/US2014/049031 dated Jan. 30, 2015 (16 pages).
International Search Report and Written Opinion for Application No. PCT/US2017/012096 (14 pages).
Lewis et al., Design and characterization of a high-power ultrasound driver with ultralow-output impedance. Rev Sci Instrum. Nov. 2009;80(11):114704.1-114704.8.
Olbricht, W., et al., "Time-reversal acoustics and ultrasound-assisted convection-enhanced drug delivery to the brain," J Acoust Soc Am. Aug. 2013; 134(2): 1569-1575.
Olbricht, William L. et al., Microfluidic Probes in the Treatment of Brain-Related Diseases, Drug News and Perspectives, 2010, 23(8)—7 pages (Oct. 2010).
Rapoport, S.I., "Osmotic opening of the blood-brain barrier: principles, mechanism, and therapeutic applications," Cell. Mol. Neurobiol. 20: 217-30 (2000).
Saltzman et al.; Building Drug Delivery Into Tissue Engineering; Nature Reviews/Drug Discovery; 2002 Macmillan Magazines Ltd.; vol. 1; Mar. 2002; pp. 177-186.
Bobo, RH, Laske, DW, Akbasak, A, Morrison, PF, Dedrick, RL, Oldfield, EH. Convection-enhanced delivery of macromolecules in the brain. Proc Natl Acad Sci U S A. Mar. 15, 1994; 91(6): 2076-2080.
Denk, W, Strickler, JH, Webb, WW. Two-photon laser scanning fluorescence microscopy. Science 248, 73-76 (1990).
Dombeck, DA, Kasischke, KA, Vishwasrao, HD, Ingelsson, M, Hyman BT, and Webb, WW. Uniform polarity microtubule assemblies imaged in native brain tissue by second-harmonic generation microscopy. Proc. Natl. Acad. Sci. 100, 7081-7086 (2003).
Foley, CP, Nishimura, N. Neeves, KB, Schaffer, CB, and Olbricht, WL. Flexible microfluidic devices supported by biodegradable insertion scaffolds for convection-enhanced neutral drug delivery. Biomed. Microdevices. 11, 1572-8781 (2009).
Guzman, HR, Nguyen, DX, McNamara, AJ Prausnitz, MR. Equilibrium loading of cells with macromolecules by ultrasound: effects of molecular size and acoustic energy. J. Pharm. Sci. 91,1693-1701 (2002).
Hall, WA, Sherr, GT. Convection-enhanced delivery: targeted toxin treatment of malignant glioma. Neurosurg Focus. 20, El 0 (2006).
Henderson, P, Lewis Jr., GK, Olbricht, WL, Spector, J, A portable high intensity focused ultrasound device for the non invasive treatment of varicose veins, J. Vas. Surg. In press (2009).
Hynynen et al. (2007). Clinical applications of focused ultrasound—The brain. Int. J Hyperth., 23, 193-202 (2007).
Hynynen K. Ultrasound for drug and gene delivery to the brain. Adv. Drug Deliv. Rev. 60, 1209-1217 (2008).
Hynynen, K, McDannold, N, Sheikov, NA, Jolesz, FA, Vykhodtseva, N. Local and reversible bloodbrain barrier disruption by noninvasive focused ultrasound at frequencies suitable for trans-skull sonications. Neuroimage. 24, 12-20 (2005).
Hynynen, K, McDannold, N, Vykhodtseva, N. Raymond, S. Weissleder, R, Jolesz, FA, Sheikov, N. Focal disruption of the blood-brain barrier due to 260-Khz ultrasound bursts: A method for molecular imaging and targeted drug delivery, J. Neurosurg. 105, 445-454 (2006).
Japanese Office Action for Application No. 2015-549618, dated Sep. 5, 2017 (12 pages).
Japanese Office Action for Application No. 2016-531883, dated Jun. 5, 2018 (10 pages).
Keyhani, K. Guzman, HR. Parsons, A, Lewis, TN, Prausnitz, MR. Intracellular drug delivery using lowfrequency ultrasound: quantification of molecular uptake and cell viability. Pharm. Res. 18,1514-1520 (2001).
Krauze, MT, Forsayeth, J, Park, JW, Bankiewicz, KS. Real-time imaging and quantification of brain delivery of liposomes. Pharm. Res. 23, 2493-2504 (2006).
Kunwar S, Prados MD, Chang SM, Berger, MS, Laff, FF. Direct intracerebral delivery of cintredekin besudotox (fL13-PE38QQR) in recurrent malignant glioma: a report by the Cintredekin Besudotox Intraparenchymal Study Group. J Clin Oncol. 25, 837-844 (2007).
Levene, MJ, Dombeck, DA, Molloy, RP, Kasischke, R, Williams, Zipfel, WR, and Webb, WW. In vivo multiphoton microscopy of deep brain tissue. J. Neurophys. 91, 1908-1912 (2004).
Mitragotri, S, Blankschtein, D, Langer, R. Ultrasound-mediated transdermal protein delivery. Science. 269, 850-853 (1995).
Morrison, PF, Chen, MY, Chadwick, RS, Lonser, RR, Oldfield, EH. Focal delivery during direct infusion to brain: role of flow rate, catheter diameter, and tissue mechanics, Am. J. Physiol. Regul. Integr. Comp. Physiol. 277 R1218 R1229.1580-1596 (1999).
Murad, GJ, Walbridge, S, Morrison, PF, et al. Real-time, image-guided, convection-enhanced delivery of imerleukin 13 bound to pseudomonas exotoxin. Clin Cancer Res. 12, 3145-3151 (2006).
Neeves, KB, Sawyer, AJ, Foley, CP, Saltzman, WM, Olbricht, WL. Dilation and degradation of the brain extracellular matrix enhances penetration of infused polymer nanoparticles. Brain Res. 1180, 121-132 (2007).
Noble, CO, Krauze, MT, Drummond, DC, Yamashita, Y, Saito, R, Berger, MS, Kirpotin, DB, Bankiewicz, KS. Novel nanoliposomal CPT-11 infused by convection-enhanced delivery in intracranial tumors: pharmacology and efficacy. Cancer Res. 66, 2801-2806 (2006).
Ohl, CD, Arora M, kink R. Sonoporation from jetting caviation bubbles. Biophys J. 91, 4285-4295 (2006).
Park, EJ, Werner, J, Smith, NB. Ultrasound mediated transdermal insulin delivery in pigs using a lightweight transducer. Pharm Res. 24, 1396-1401 (2007).
Raghavan R, Brady ML, Rodriguez-Ponce MI, Hartlep A, Pedain C, Sampson JH. Convection-enhanced delivery of therapeutics for brain disease, and its optimization. Neurosurg Focus. 20, El 2 (2006).
Reddy ST, Berk, DA, Jain, RK, Swartz, MA. A sensitive in vivo model for quantifying interstitial convective transport of injected macromolecules and nanoparticles. J Appl Physiol. 101, 1162-1169 (2006).
Ren, H, Boulikas, T, Soling, A, Warnke, PC, Rainov, NG. Immunogene therapy of recurrent glioblastoma multiforme with a liposomally encapsulated replication-incompetent semliki forest virus vector carrying the human interleukin-12 gene a phase i/ii clinical protocol. J. Neuro-oncol. 64, 147-154 (2003).
Samtinoranont, M, Chen, X, Zhao, J, Mareci, TH. Computational model of interstitial transport in the spinal cord using diffusion tensor imaging. Aim, Biomed, En g. 34, 1304-1321 (2006).
Shimamura, T, Husain SR, Puri, RK. The IL-4 and IL-13 pseudomonas exotoxins: new hope for brain tumor therapy. Neurosurg Focus. 20, Ell (2006).
Smith, NB, Lee, S, Shung, K. Ultrasound-mediated transdermal in vivo transport of insulin with low-profile cymbal arrays. J. Ultra. Med. Bio. 29, 1205-1210 (2003).
Squirrell, JM, Wokosin, DL, White, JG, Bavister, BD. Long-term two-photon fluorescence imaging of mammalian embryos without compromising viability. Nat Biotechnol. 17, 763-7 (1999).
Sundaram, J, Mellein, BR, Mitragotri, S. An experimental and theoretical analysis of ultrasound-induced permeabilization of cell membranes. Biophys. J. 84, 3087-3101 (2003).
Vogelbaum MA. Convection enhanced delivery for treating brain tumors and selected neurological disorders: symposium review. J Neurooncol. 83, 97-109 (2007).
Yamashita, Y, Krauze, MT, Kawaguchi, T, Noble, CO, Drummond, DC, Park, JW, Bankiewicz, KS. Convection-enhanced delivery of a topoisomerase I inhibitor (nanoliposomal topotecan) and a topoisomerase II inhibitor (pegylated liposomal doxorubicin) in intracranial brain tumor xenografts. Neuro Oncol. 9, 20-28 (2007).
Yang, W, Barth, RF, Adams, DM, Ciesielski, MJ, Fenstermaker, RA, Shulda, S, Tjarks, W, Cligiuri, MA. Convection-enhanced delivery of boronated epidermal growth factor for molecular targeting of egf receptorpositive gliomas. Cancer Res. 62, 6552-6558 (2002).
Zipfel, WR, Williams, RM, Christie, R, Nikitin, AY, Hyman, BT, and Web, WW. Live tissue intrinsic emission microscopy using

(56) References Cited

OTHER PUBLICATIONS multiphoton-excited native fluorescence and second harmonic generation. Proc. Nat. Acad. Sci. 100, 7075-7080 (2003).

* cited by examiner

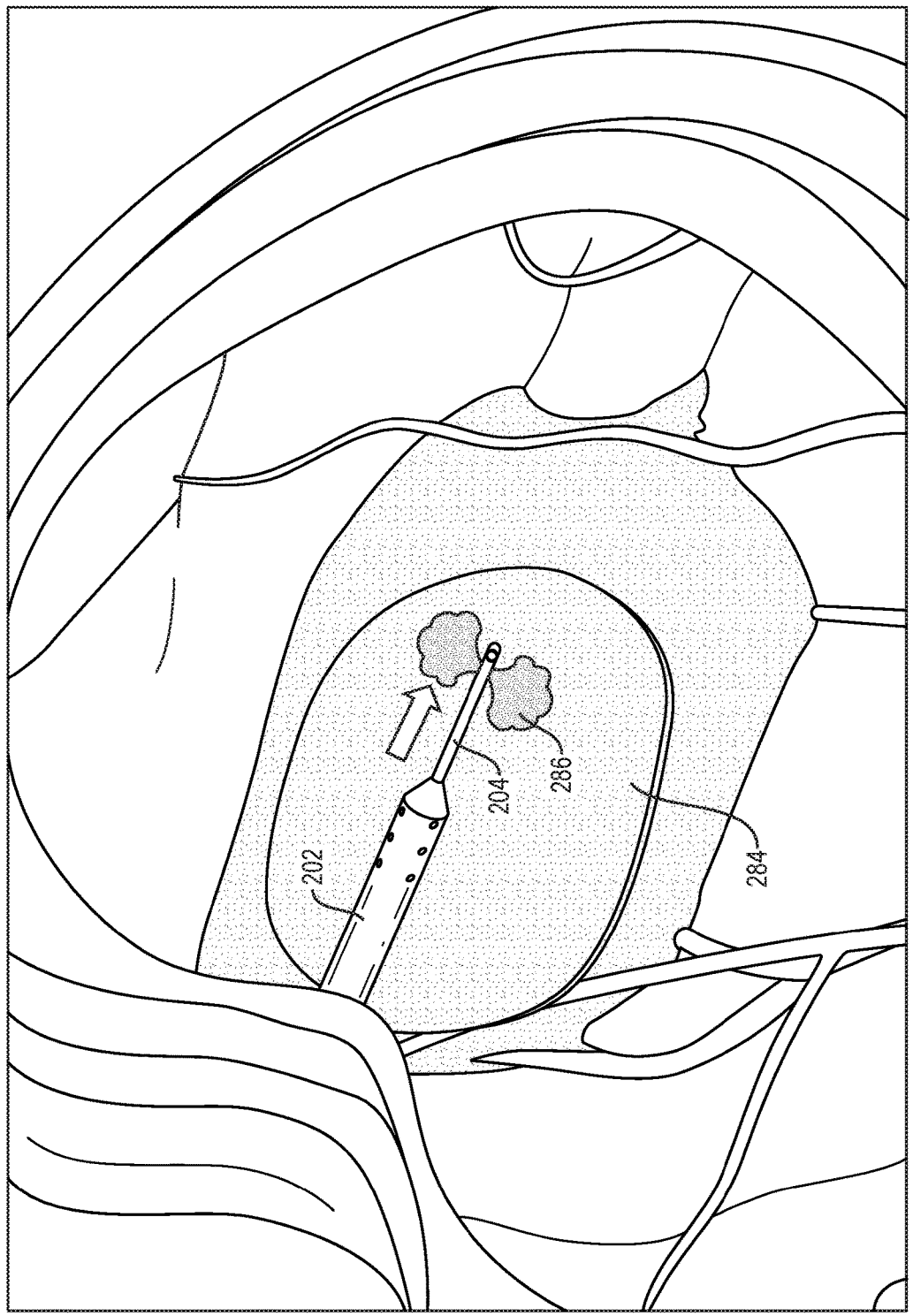

METHODS AND DEVICES FOR TREATING STROKE

CROSS-REFERENCE TO RELATED APPLICATIONS

This application claims priority to U.S. Provisional Application No. 62/274,582 filed on Jan. 4, 2016 and entitled "METHODS AND DEVICES FOR TREATING STROKE," which is hereby incorporated by reference in its entirety.

FIELD

Methods and devices for delivering a drug to a subject and for aspirating material from the subject are disclosed herein, e.g., for the treatment of stroke.

BACKGROUND

Millions of people are affected by strokes each year and strokes are a leading cause of disability and death. The damage caused by a stroke can be reduced by early and efficient treatment. Existing stroke treatments, however, can be suboptimal. For example, one treatment method is to insert a ventricular drain into the patient's brain to relieve pressure and drain blood that has collected in the brain as a result of the stroke. A thrombolytic agent such as tissue plasminogen activator (tPA) can be administered to the patient to help break up blood clots and the allow the clots to drain out. This treatment method requires the thrombolytic to be delivered very slowly and the drain must remain in the patient for an extended period of time (e.g., many hours or days), which lengthens time spent in surgery or the intensive care unit and results in suboptimal patient outcomes. There is a continual need for improved methods and devices for treating stroke.

SUMMARY

Methods and devices are disclosed herein that allow for infusion and aspiration through a single device. The device can be used to treat a stroke by delivering the device to the site of a blood clot and simultaneously or sequentially infusing a thrombolytic or other drug into the clot and aspirating the dissolving clot from the patient. The methods and devices can advantageously permit more efficient thrombolytic infusion and clot aspiration. Modular systems are also disclosed, as are methods of treating subdural hematoma or other conditions.

In some embodiments, a catheter system includes an infusion catheter having an infusion lumen and at least one outlet port; and an aspiration catheter having an aspiration lumen and at least one aspiration port, the aspiration catheter defining a channel in which the infusion catheter is slidably disposed.

The aspiration catheter can define a bullet-nose feature. The system can include an insertion stylet removably positioned in the infusion lumen of the infusion catheter. The system can include a TRA system. The TRA system can include a hydrophone or microphone disposed in a distal end of the infusion catheter, one or more leads extending from the hydrophone or microphone to a proximal end of the infusion catheter, and a reverberator configured to time-reverse a signal detected by the hydrophone or microphone and emit acoustic waves based on the time-reversed signal. The aspiration catheter can include first and second steering wires to which tension can be applied to remotely steer a distal end of the aspiration catheter. The aspiration lumen can include first and second aspiration lumens, each having a C-shaped transverse cross-section.

In some embodiments, a method of treating a patient includes advancing a catheter system to a treatment site within the patient; delivering at least one of a drug and an irrigation fluid to the treatment site through an infusion catheter of the catheter system; advancing an aspiration catheter of the catheter system distally with respect to the infusion catheter; and aspirating material from the treatment site through an aspiration lumen of the aspiration catheter.

The treatment site can include a clot in a brain of the patient. The drug can include a thrombolytic. The aspirated material can include clot material. Aspirating the material can include steering the aspiration catheter within the treatment site. Delivering the drug can include enhancing diffusion rate of the drug by applying acoustic energy to the treatment site. Delivering the drug can include controlling the direction in which the drug is distributed using acoustic energy. The acoustic energy can be emitted from a TRA system.

In some embodiments, a modular catheter system includes an aspiration catheter having a proximal aspiration housing with an aspiration port formed therein; an infusion catheter slidably disposed within the aspiration catheter and having a proximal infusion housing with an infusion port formed therein; and a cap housing configured to be selectively coupled to either of the aspiration housing and the infusion housing.

The system can include an insertion stylet having a proximal insertion housing configured to be selectively coupled to the infusion housing. The aspiration housing and the infusion housing can define a catheter module and the system can include a hand control module configured to be selectively coupled to the catheter module. The hand control module can include a control for advancing or retracting the infusion catheter relative to the aspiration catheter. The hand control module can include a control for steering the aspiration catheter. The aspiration housing and the infusion housing can define a catheter module and the system can include a stereotactic module configured to be selectively coupled to the catheter module. The stereotactic module can include a mating feature for attaching the stereotactic module to a stereotactic frame. The stereotactic module can include a first control for advancing or retracting the infusion catheter relative to the aspiration catheter and a second control for steering the aspiration catheter.

BRIEF DESCRIPTION OF THE DRAWINGS

The following detailed description is provided in conjunction with the accompanying drawings, in which:

FIG. 6C is a schematic view of the hematoma of FIG. 6A with the catheter system of FIG. 5A infusing a fluid into the hematoma;

DETAILED DESCRIPTION

Figure 1:
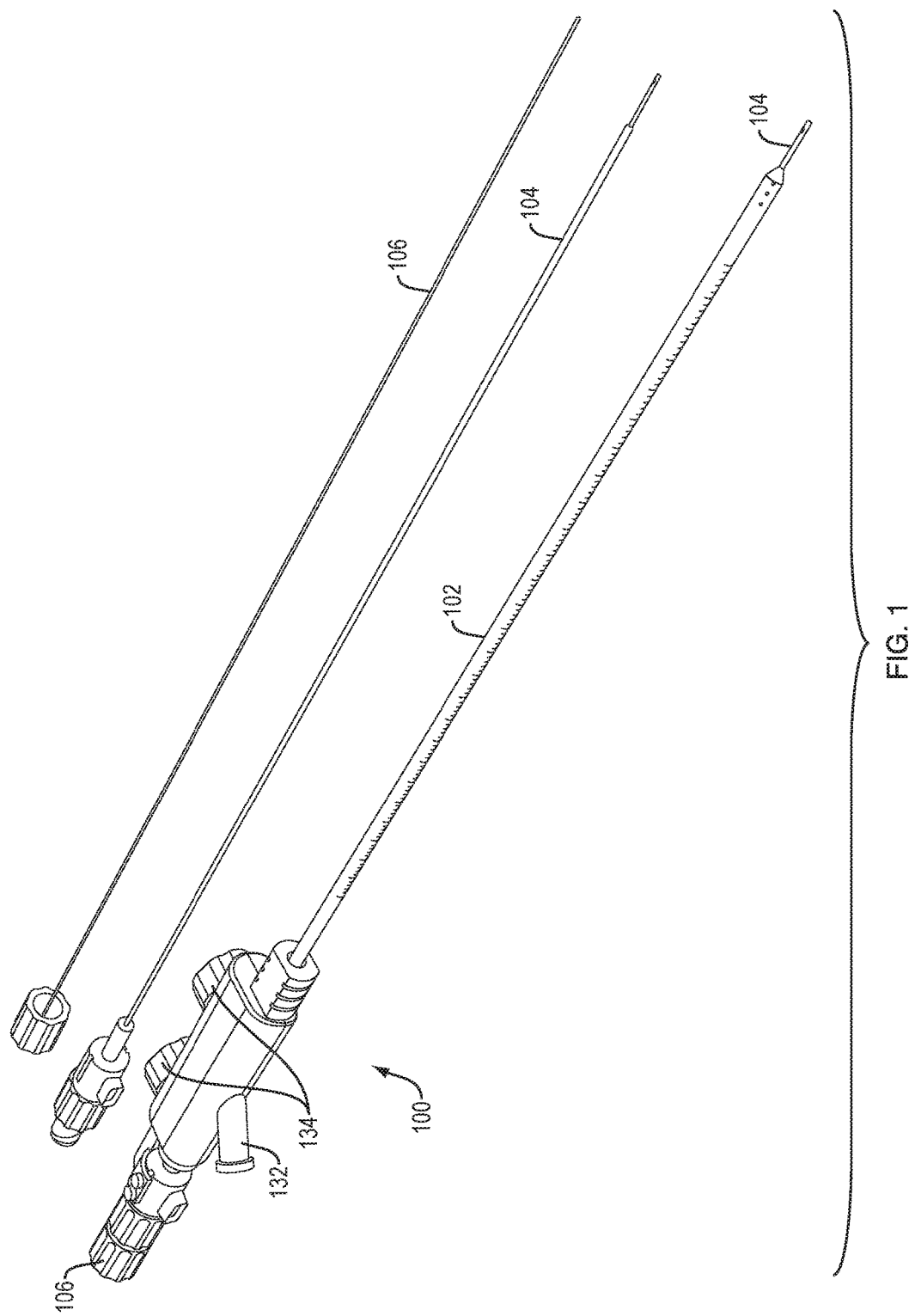
FIG. 1 is a perspective view of an exemplary catheter system, shown in assembled form and with an extra infusion lumen and insertion stylet.

Methods and devices are disclosed herein that allow for infusion and aspiration through a single device. The device can be used to treat a stroke by delivering the device to the site of a blood clot and simultaneously or sequentially infusing a thrombolytic or other drug into the clot and aspirating the dissolving clot from the patient. The methods and devices can advantageously permit more efficient thrombolytic infusion and clot aspiration. Modular systems are also disclosed, as are methods of treating subdural hematoma or other conditions.

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure.

FIGS. 1-3C illustrate an exemplary embodiment of a catheter system 100. As shown, the system 100 can include an aspiration catheter 102 and an infusion catheter 104. The system 100 can also include a removable insertion stylet 106.

The system 100 can include a time reversal acoustics (TRA) module 108 or other device for focusing acoustic energy (e.g., ultrasound energy) to enhance or control infusion. In an exemplary TRA system, a hydrophone at the distal end of the catheter measures an acoustic signal at the drug delivery site. The sensed acoustic signal is communicated through a wired or wireless interface to a processor or circuit that time reverses the acoustic signal. The time-reversed acoustic signal is then used to drive a reverberator placed external to the patient. The acoustic energy applied by the reverberator can be used to enhance or quicken the infusion of the drug and/or control the direction in which the drug is infused. Further details on TRA and drug delivery can be found in OLBRICHT, W. et al., TIME-REVERSAL ACOUSTICS AND ULTRASOUND-ASSISTED CONVECTION-ENHANCED DRUG DELIVERY TO THE BRAIN, J Acoust Soc Am. 2013 August; 134(2):1569-75, which is hereby incorporated by reference herein.

Figure 2:
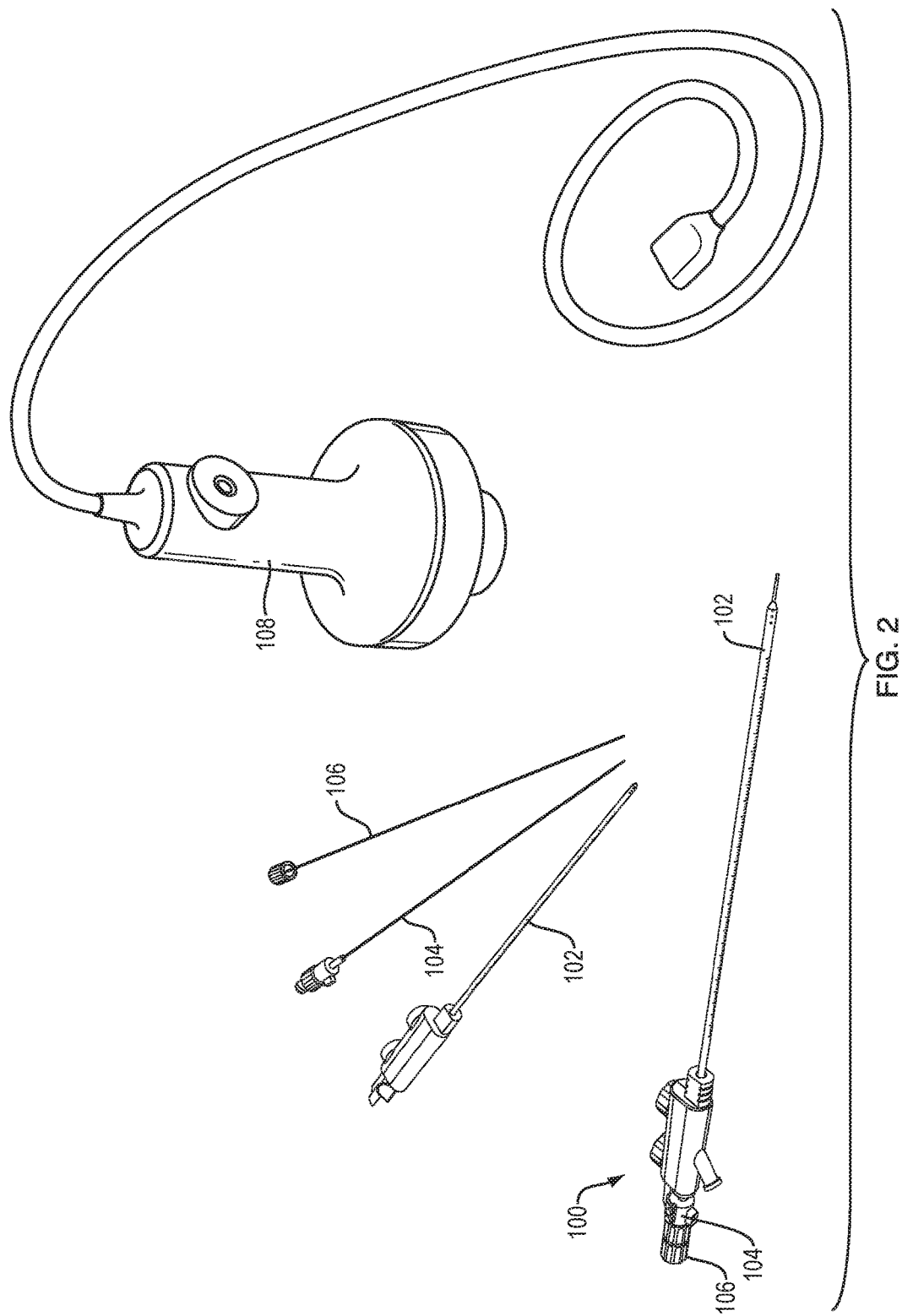
FIG. 2 is a perspective view of the catheter system of FIG. 1, in exploded and assembled configurations and shown with a TRA module.

As shown in FIG. 2, the insertion stylet 106 can be inserted through a lumen of the infusion catheter 104 and the infusion catheter and stylet can be inserted through a lumen of the aspiration catheter 102.

Figure 3A:
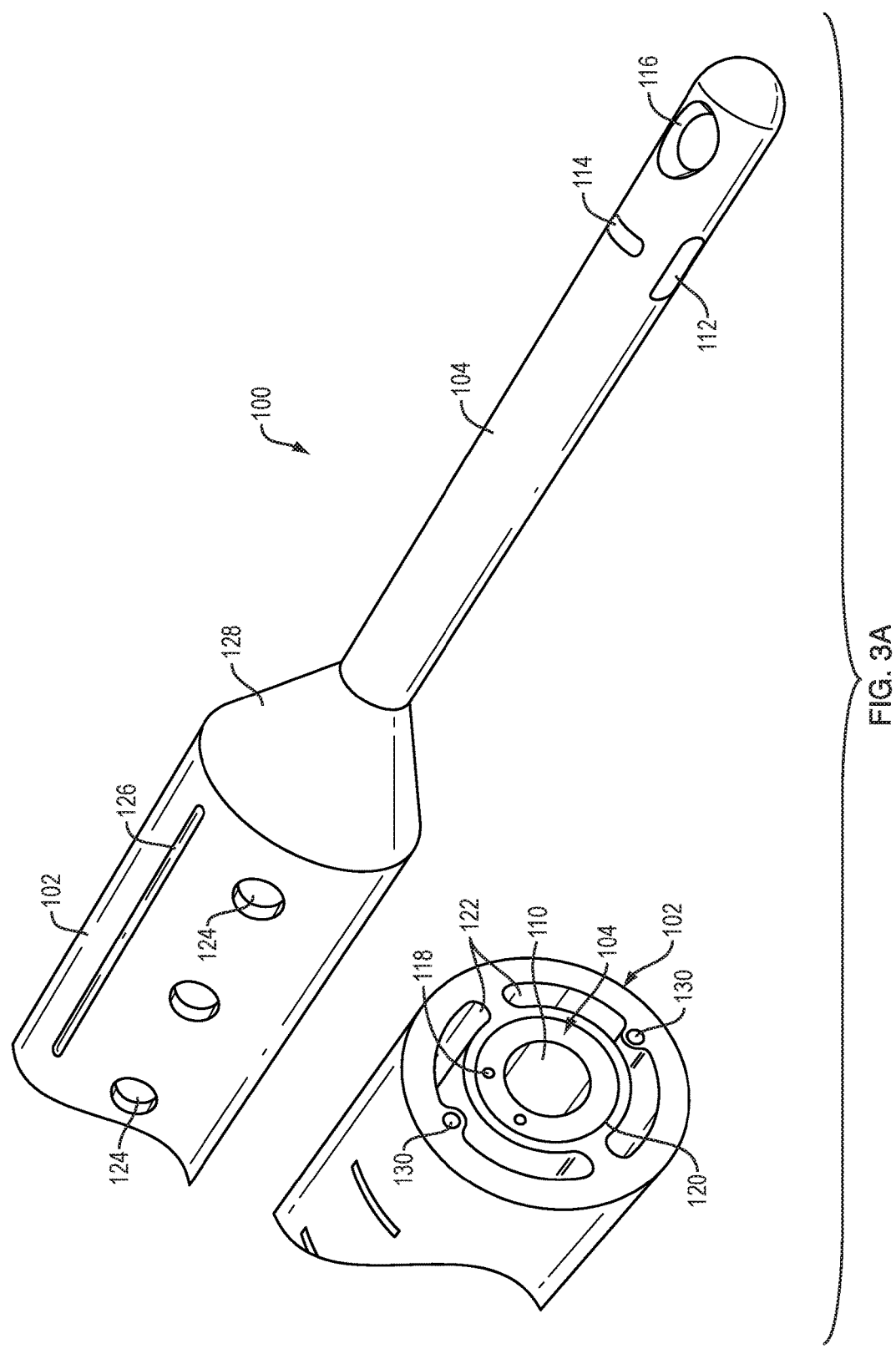
FIG. 3A is an enlarged perspective view and an enlarged sectional view of the distal end of the catheter system of FIG. 1.

Referring to FIG. 3A, the infusion catheter 104 can include an elongate tubular body that defines a central fluid lumen 110. The infusion catheter 104 can include one or more fluid outlet ports 112, which can be formed at any of a variety of locations on the catheter. In the illustrated embodiment, the fluid outlet ports 112 are formed in lateral sidewalls of the catheter 104. The catheter 104 can include first and second diametrically opposed side exit fluid outlet ports 112 formed adjacent a distal end thereof. The infusion catheter 104 can include one or more radiopaque markers 114 to facilitate visualization during a surgical procedure, e.g., via fluoroscope, CT, MRI, or PET imaging. A MEMS hydrophone or a micro hydrophone 116 can be disposed adjacent a distal end of the infusion catheter 104 for detecting an acoustic signal for use in the TRA system 108 described above. One or more electrical leads 118 for communicating the detected acoustic signal to a proximal end of the catheter 104 and the other components of the TRA system 108 can be embedded in a sidewall of the infusion catheter 104 or threaded through the central lumen 110 of the catheter.

As also shown in FIG. 3A, the aspiration catheter 102 can include an elongate tubular body that defines a central lumen 120 in which the infusion catheter 104 is disposed. The infusion catheter 104 can be longitudinally-translatable within the central lumen 120 relative to the aspiration catheter 102. The aspiration catheter 102 can include one or more aspiration lumens 122 through which dissolved clots or other material can be extracted from a treatment site. In the illustrated embodiment, the aspiration catheter 102 includes first and second aspiration lumens 122 having C-shaped transverse cross-sections disposed on either side of the central lumen 120. It will be appreciated that the aspiration lumens 122 can have any of a variety of other shapes and configurations. The aspiration lumens 122 can be in fluid communication with an exterior of the aspiration catheter 102 via one or more aspiration ports 124, which can be formed in a lateral sidewall of the aspiration catheter as shown.

The aspiration catheter 102 can include one or more radiopaque markers 126 to facilitate visualization during a surgical procedure. A distal end of the aspiration catheter 102 can have a tapered, ramped, or bulleted shape 128 that provides a gradual transition from the larger external diameter of the aspiration catheter to the smaller external diameter of the infusion catheter 104. This shape can advantageously form a seal with surrounding tissue in which the system 100 is inserted to prevent backflow of infusate along the insertion track of the catheters 102, 104 and thereby substantially contain infused drug to the distal end of the infusion catheter and its general vicinity. The system 100 can include other features for reducing or preventing backflow, such as an overtube that defines a tissue-receiving space configured to pinch tissue and form a seal therewith, for example as disclosed in U.S. Pat. No. 8,992,458 entitled "SYSTEMS AND METHODS FOR REDUCING OR PREVENTING BACKFLOW IN A DELIVERY SYSTEM" which is hereby incorporated by reference herein. Exemplary bullet-nose features are also disclosed in this reference.

The aspiration catheter 102 can include a mechanism for remotely steering the distal end of the catheter within a treatment site. In the illustrated embodiment, the aspiration catheter 102 includes first and second diametrically opposed steering wires 130 embedded in sidewalls of the catheter. Tension can be applied to proximal ends of the steering wires 130 disposed external to the patient to steer the distal end of the catheter 102 within the treatment site.

Figure 3B:
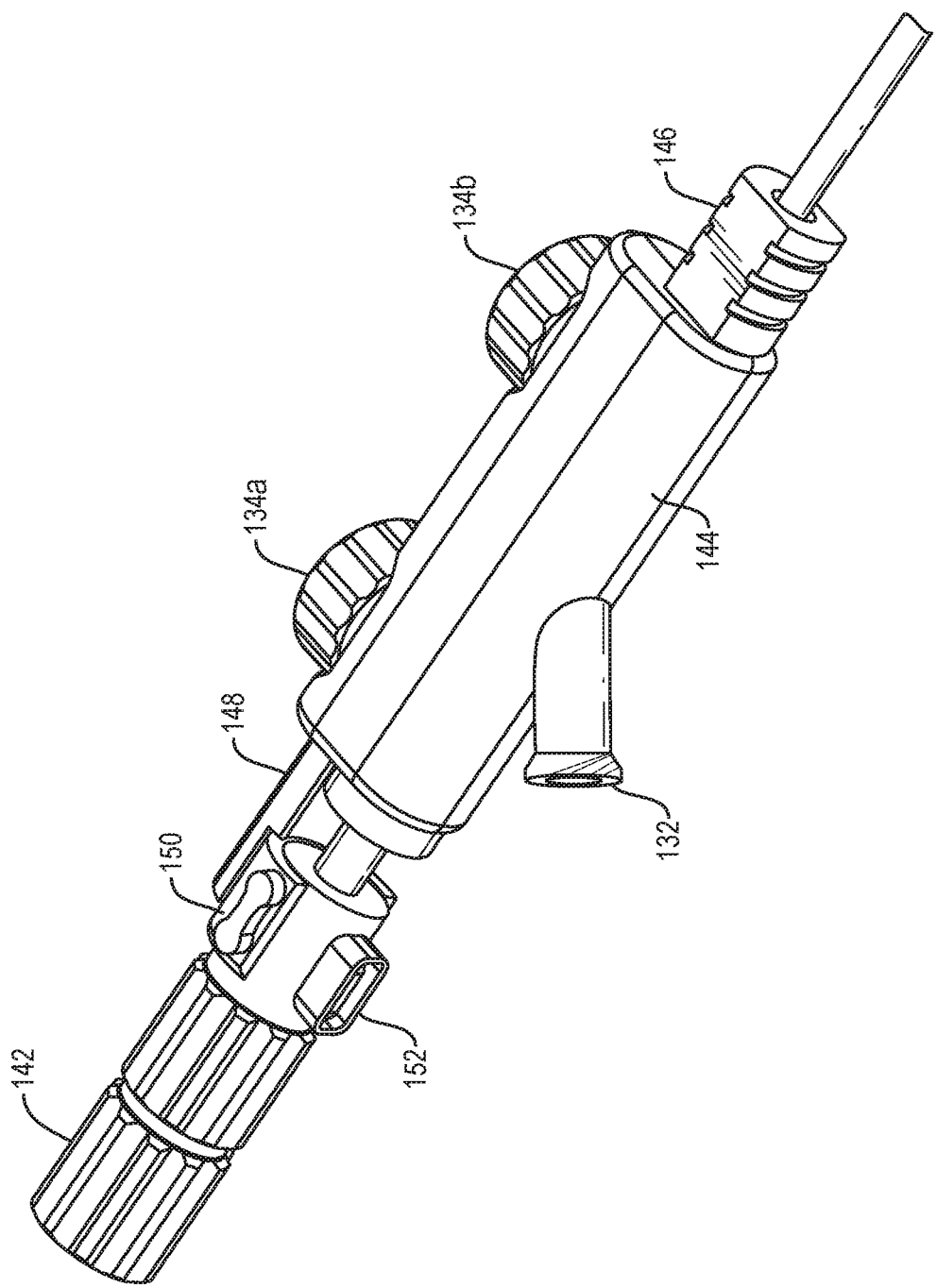
FIG. 3B is an enlarged perspective view of the proximal end of the catheter system of FIG. 1.
Figure 3C:
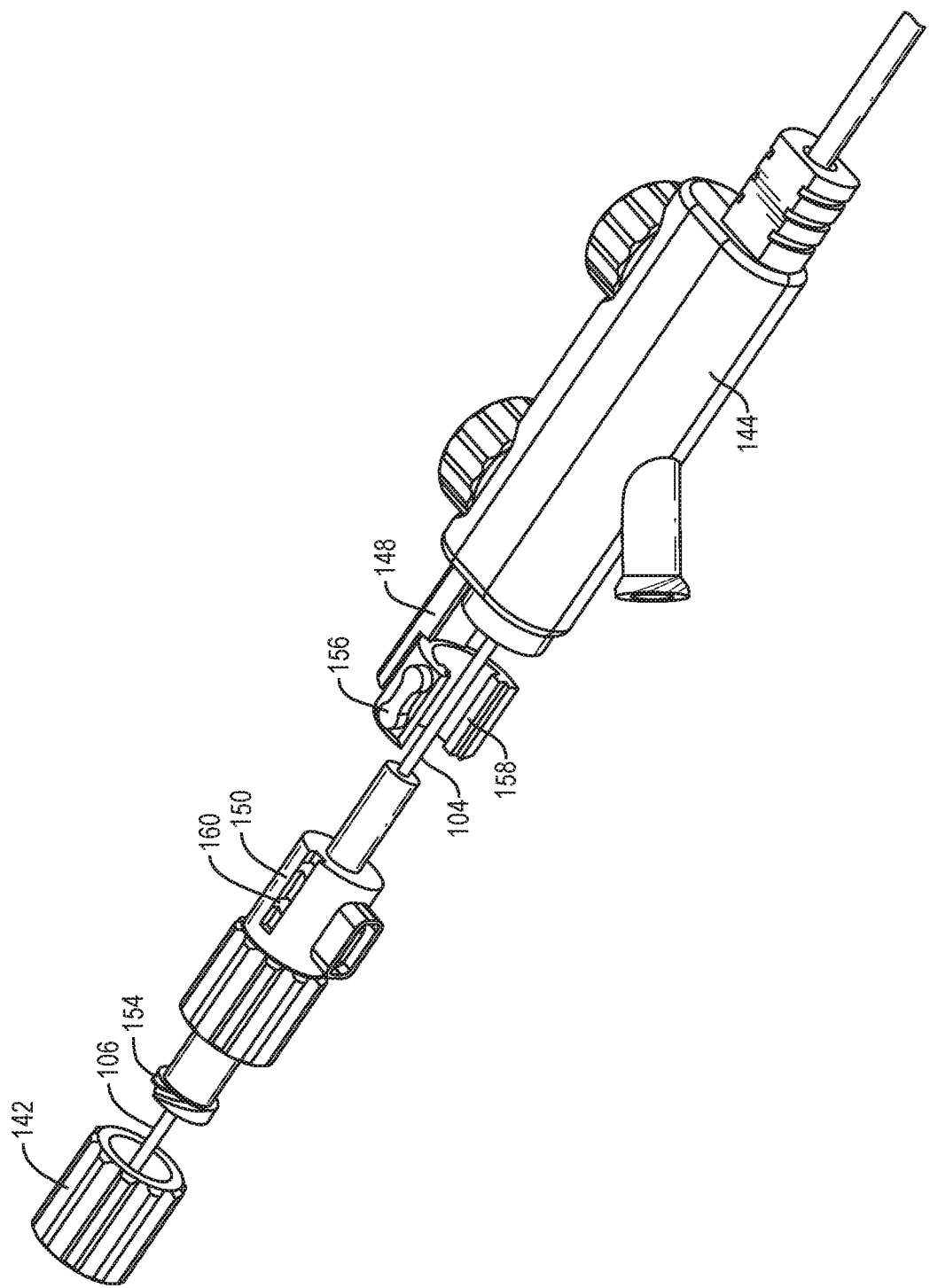
FIG. 3C is an enlarged exploded view of the proximal end of the catheter system of FIG. 1.

The aspiration catheter 102 can include an aspiration port 132 through which the catheter can be connected to a vacuum pump or other aspiration source. The system 100 can include various controls 134 for operating the system. For example, as shown in FIGS. 3B-3C, the system can include a first knob 134A configured to control extension and retraction of the infusion catheter 104 relative to the aspiration catheter 102. The first knob 134A can be coupled to a wheel that frictionally engages or otherwise mechanically engages the infusion catheter 104 such that rotation of the knob 134A causes the infusion catheter 104 to translate longitudinally with respect to the aspiration catheter 102. Alternatively, as shown, the first knob 134A can be engaged with a beam 148 slidably mounted to a housing 144 of the aspiration catheter 102. A proximal portion of the beam 148 can be selectively attached to a mounting body 150 of the infusion catheter 104. For example, the beam 148 can include a C-shaped clip 156 configured to fit around the mounting body 150. The clip 156 can include opposed ridges 158 that engage corresponding grooves 160 of the mounting body 150 to releasably retain the clip to the mounting body. The ridges 158 and grooves 160 can be keyed such that relative longitudinal movement between the clip 156 and the mounting body 150 is prevented when the ridges and grooves are mated. It will be appreciated that the ridges and grooves can be interchanged, e.g., such that the grooves are formed in the clip 156 and the ridges are formed in the mounting body 150. Rotation of the first knob 134A can be effective to translate the beam 148, and the mounting body 150 and infusion catheter 104 by extension, longitudinally with respect to the aspiration catheter 102 to advance or retract the infusion catheter relative to the aspiration catheter. The mounting body 150 of the infusion catheter 104 can include a connector 152 for establishing an electric, acoustic, and/or optical connection between the hydrophone 116 and the TRA system 108.

The system 100 can include a second knob 134B configured to control steering of the aspiration catheter 102. The second knob 134B can be rotated to selectively apply tension to the steering wires 130 to steer the aspiration catheter 102. The system can also include controls for selectively and/or individually applying aspiration to the first and second aspiration lumens 122.

The removable insertion stylet 106 shown in FIGS. 1-2 can be selectively positioned within the central lumen 110 of the infusion catheter 104 to facilitate insertion and targeting of the catheter system 100. The stylet 106 can include an attachment cap 142 at a proximal end thereof. The cap 142 can facilitate grasping of the stylet 106 by a user and can be used to attach the stylet to the infusion catheter 104 or the aspiration catheter 102, e.g., via a threaded or snap-fit coupling formed around or adjacent to a proximal infusion port 154 of the infusion catheter.

A proximal end of the aspiration catheter 102 can include a body or housing 144. The housing 144 can include a mounting block 146 to facilitate attachment of the housing to a stereotactic frame.

FIGS. 4A-4E illustrate an exemplary method of using the system 100 to deliver a drug to a patient and remove a clot from the patient, e.g., to treat stroke.

Figure 4A:
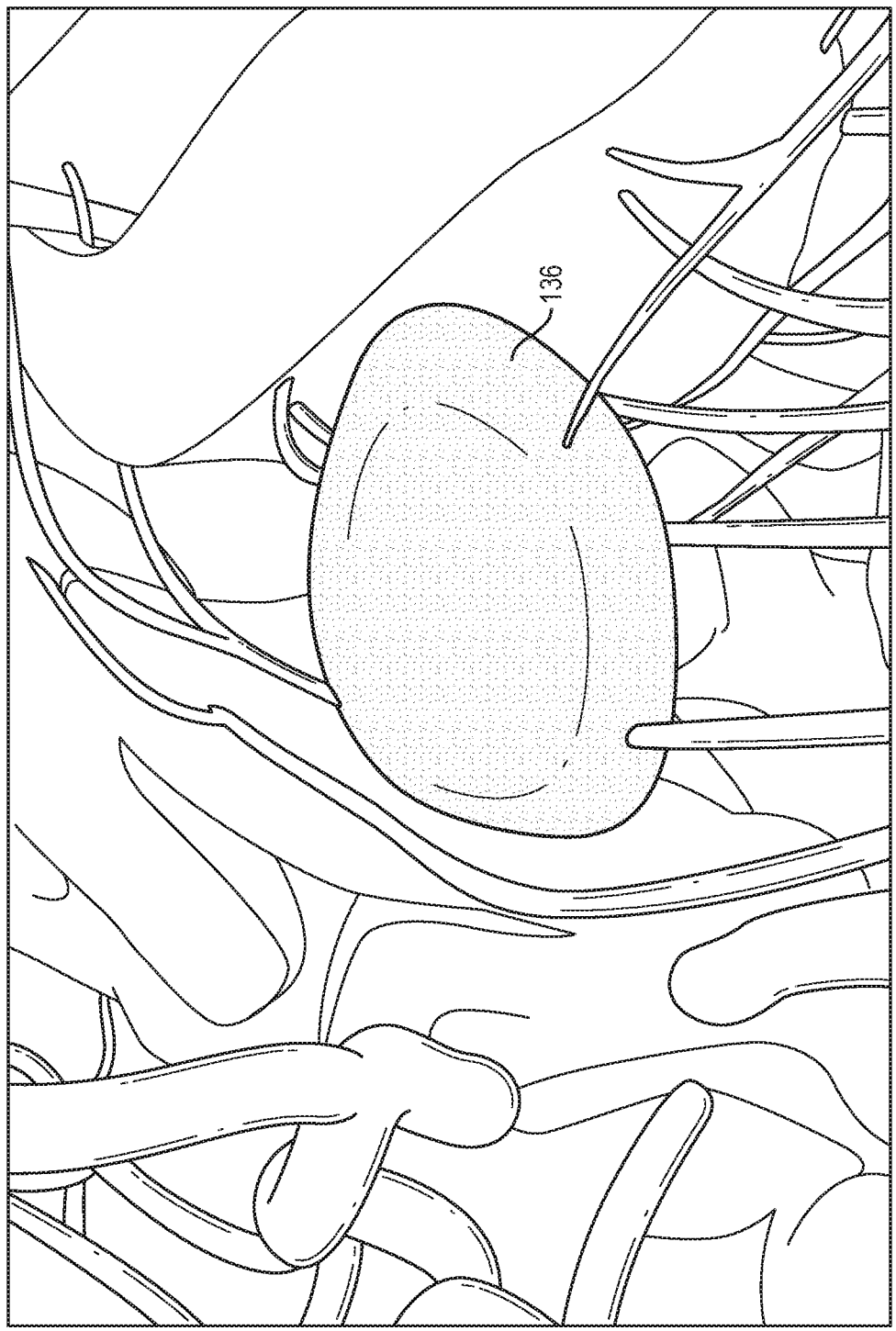
FIG. 4A is a schematic view of a clot.

As shown in FIG. 4A, the site of a clot or hemorrhage 136 can be located within the patient (e.g., within the patient's brain) and a stereotactic approach to the site can be planned.

Figure 4B:
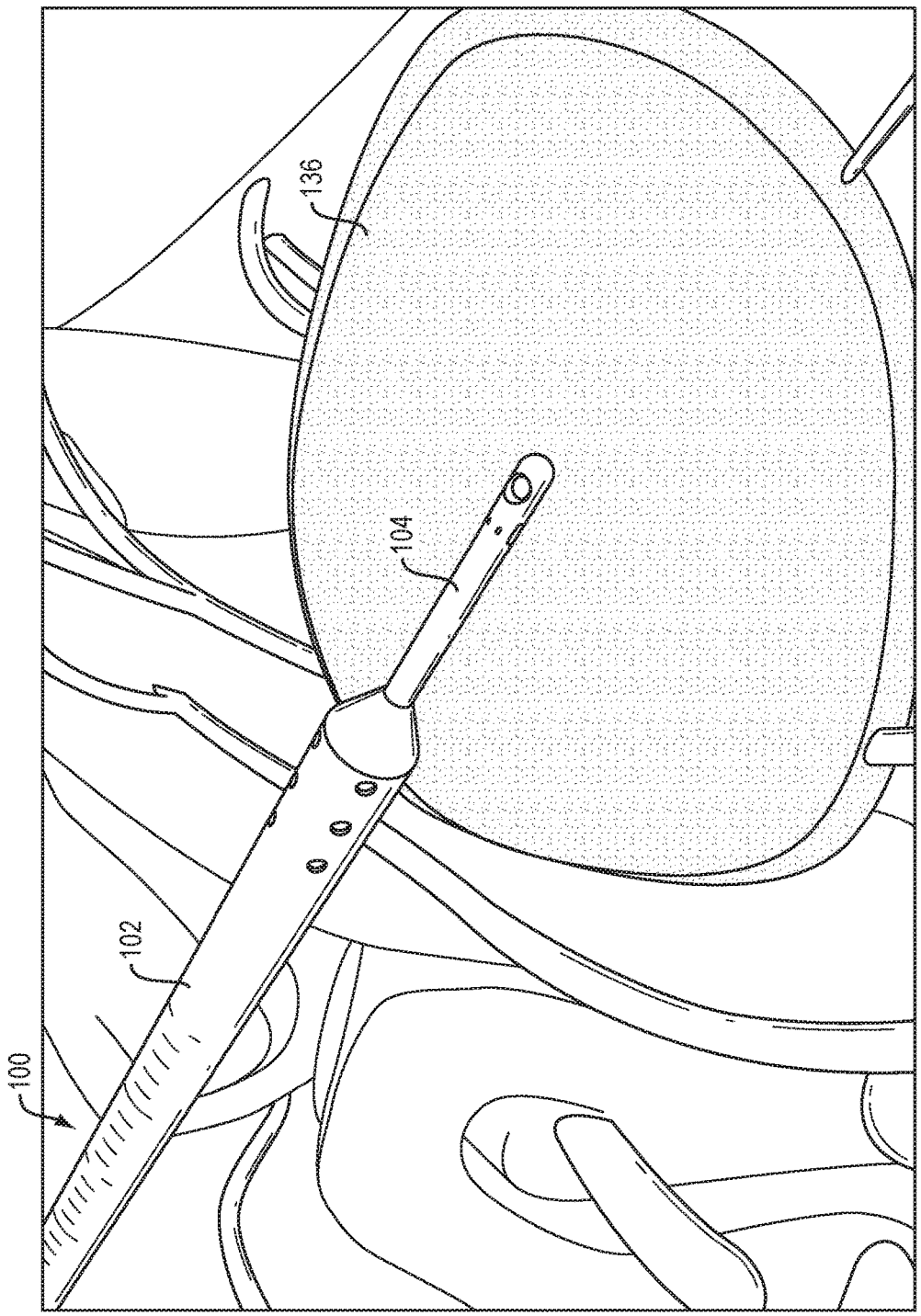
FIG. 4B is a schematic view of the clot of FIG. 4A with the catheter system of FIG. 1 inserted into the clot.

The catheter system 100 can then be guided to the site 136, e.g., using stereotactic navigation, as shown in FIG. 4B. Once at the site, or at any other desired time, the insertion stylet 106 can be removed from the catheter system 100.

Figure 4C:
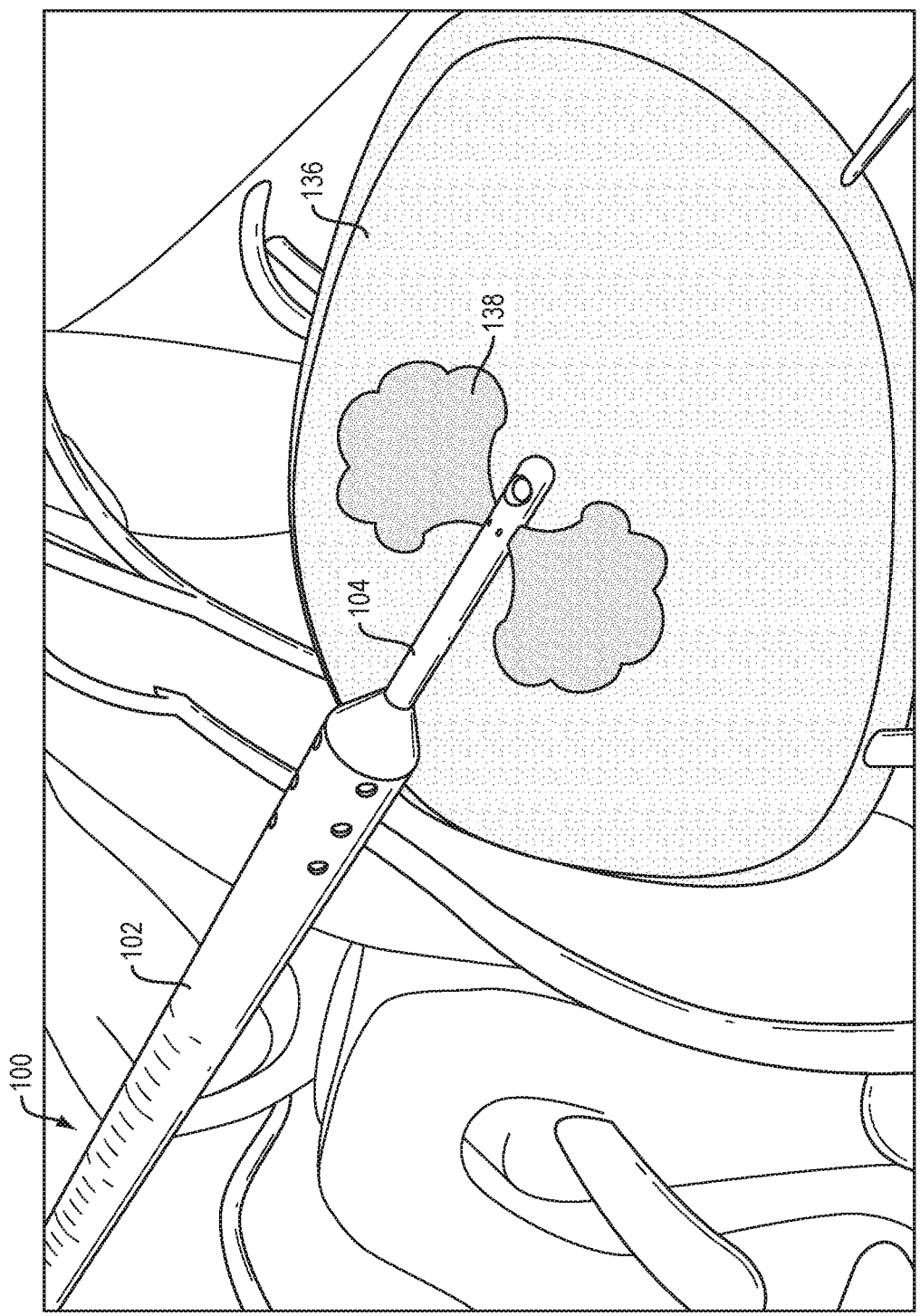
FIG. 4C is a schematic view of the clot of FIG. 4A with the catheter system of FIG. 1 infusing a fluid into the clot.

As shown in FIG. 4C, a drug 138 can be infused through the infusion catheter 104 to the target site 136. The term "drug" as used herein refers to any functional agent that can be delivered to a human or animal patient, including hormones, stem cells, gene therapies, chemicals, compounds, small and large molecules, dyes, antibodies, viruses, therapeutic agents, etc. The drug can be or can include a thrombolytic agent (e.g., tPA). Alternatively, or in addition, an irrigation fluid such as saline can be delivered through the infusion catheter 104.

Figure 4D:
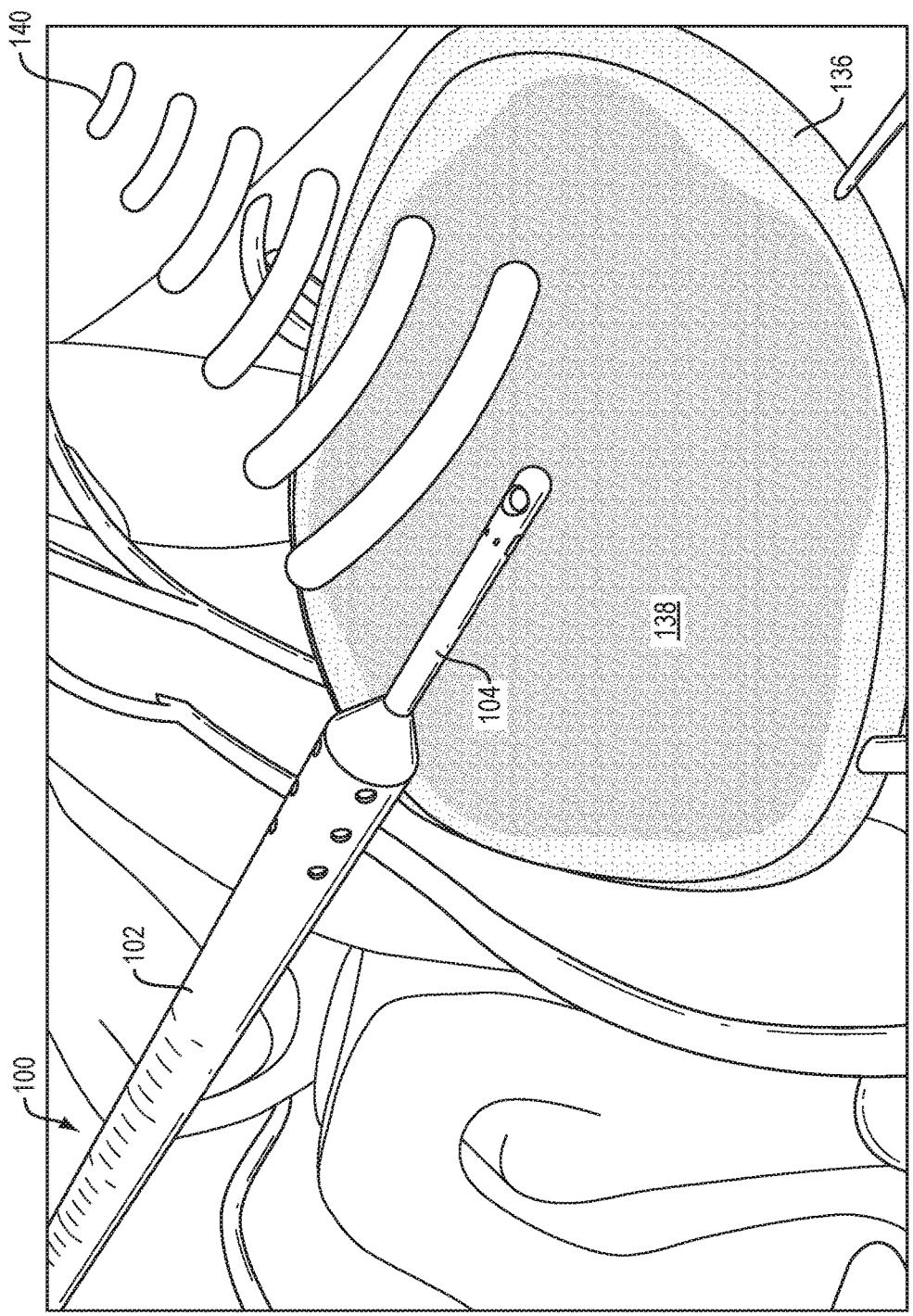
FIG. 4D is a schematic view of the clot of FIG. 4A with the catheter system of FIG. 1 applying ultrasound energy to the clot.

As the drug 138 is infused through the infusion catheter 104, the TRA module 108 can be actuated to deliver focused acoustic energy 140 to the target site 136 and thereby rapidly diffuse the drug 138 throughout the clot and/or control the direction of drug diffusion, as shown in FIG. 4D.

Figure 4E:
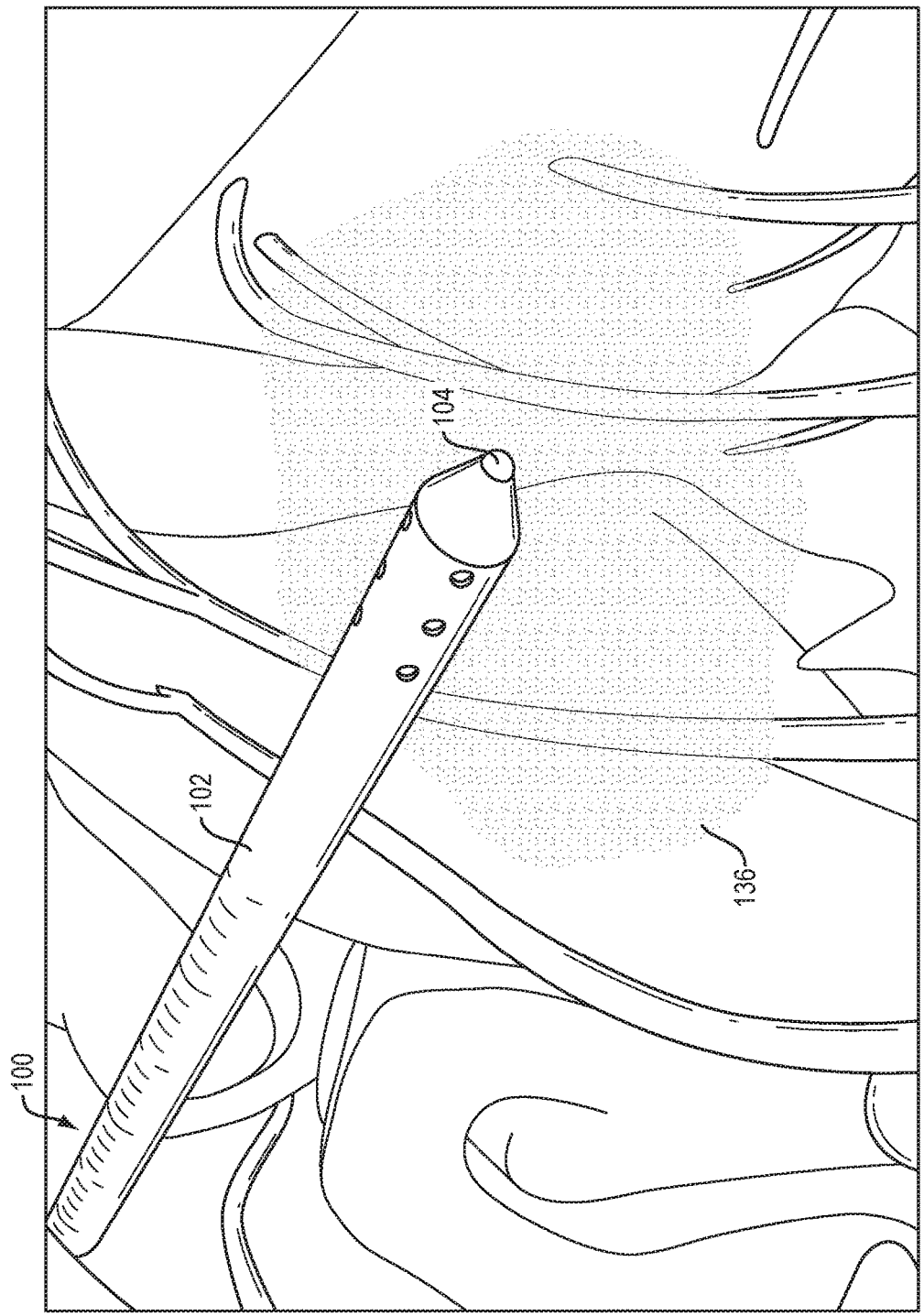
FIG. 4E is a schematic view of the clot of FIG. 4A being aspirated through the catheter system of FIG. 1.

As shown in FIG. 4E, the aspiration catheter 102 can be advanced distally over the infusion catheter 104 and into the clot 136 to aspirate the clot material as it dissolves. The distal end of the aspiration catheter 102 can be steered within the treatment site 136 to ensure that all of the clot material is aspirated. For example, the steering wires 130 of the aspiration catheter 120 can be actuated to sweep the catheter tip back and forth within the treatment site 136. Irrigation fluid can be delivered to the treatment site 136 to flush out the clot material. Once the clot is removed, or at any other desired time, the system 100 can be removed from the patient. As discussed below, one or more components of the system, e.g., the aspiration catheter 102, can be left in place for long-term drainage over a period of hours, days, or weeks.

In some embodiments, one or more components of the system can be modular. A modular catheter system can accommodate various different workflows. For example, a stylet, infusion, and aspiration assembly can be used to place the catheter, the stylet can then be removed and the end capped for infusion/irrigation and TRA ultrasound, then the infusion module can be removed, leaving a compact drain module for longer term drainage where necessary or desirable.

FIGS. 5A-5F illustrate an exemplary modular catheter system 200. Except as described herein and as will be readily appreciated by one having ordinary skill in the art, the catheter system 200 of FIGS. 5A-5F can be substantially similar to the catheter system 100 described above. Accordingly, a detailed description of the structure and function of the catheter system of FIGS. 5A-5F is omitted here for the sake of brevity.

Figure 5A:
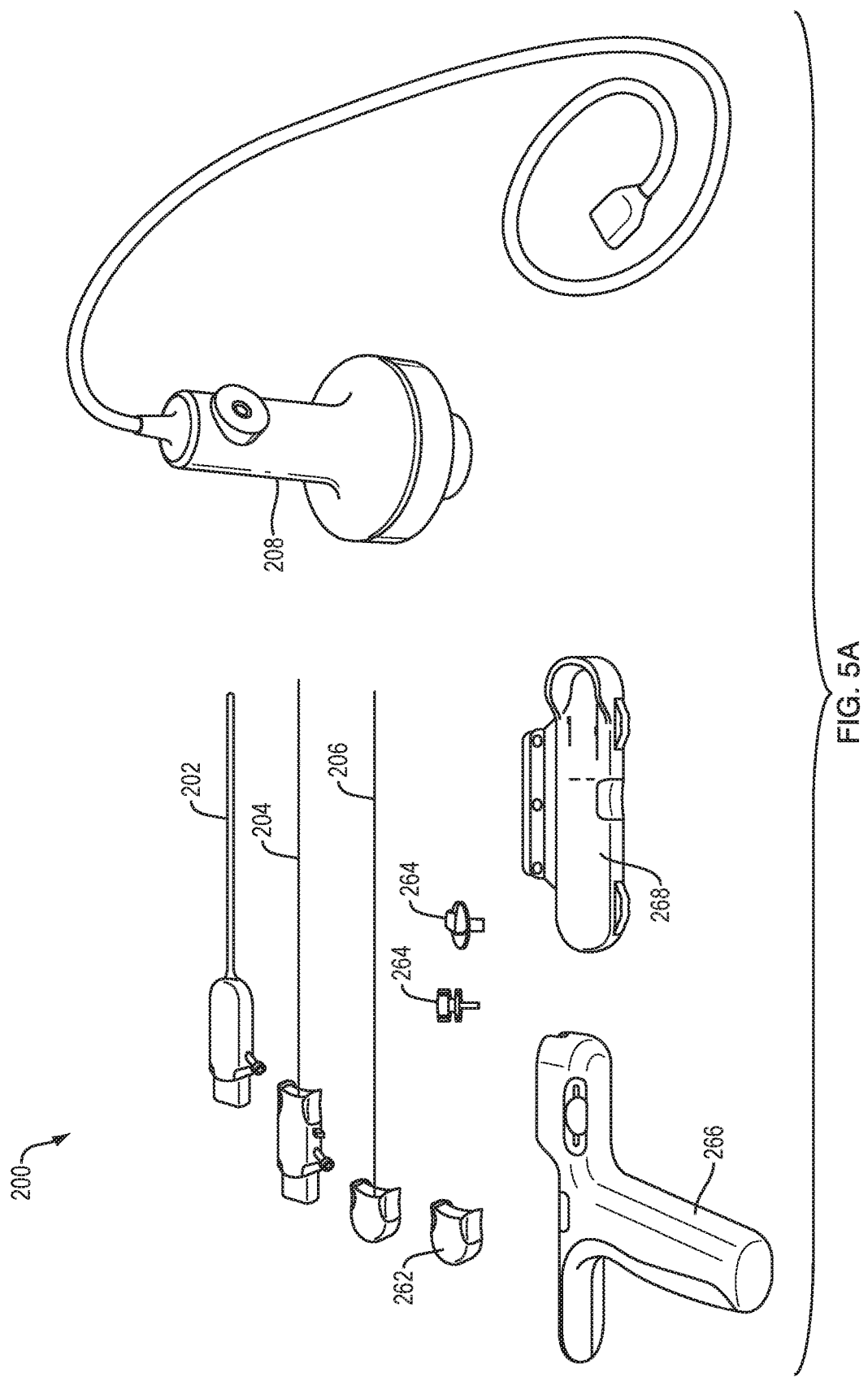
FIG. 5A is a perspective view of an exemplary modular catheter system, shown in a disassembled state and with a TRA module.

Referring to FIG. 5A, the system 200 can include an aspiration catheter 202 and an infusion catheter 204. The system 200 can include a stylet 206 insertable through the catheters 202, 204 to facilitate insertion of the system into a patient. The system 200 can include a cap 262 to cap off a proximal end of the system, e.g., when the stylet 206 or infusion catheter 204 is removed. The system can include one or more skull anchors or catheter guides 264 for securing the system to a patient or for guiding the catheter. The system 200 can include a hand control module 266 to provide single-handed, ambidextrous operation of the system controls, providing for efficient hand-guided procedures. The system 200 can include a low-profile stereotactic module 268 to provide controls in a compact platform for integration into stereotactic navigation systems. The system 200 can include a TRA module 208 or other device for focusing acoustic energy (e.g., ultrasound energy) to enhance or control infusion.

As shown, the coaxial stylet 206, infusion catheter 204, and aspiration catheter 202 can be substantially the same as in the system 100. In the system 200, however, each catheter's proximal end terminates in a modular cartridge housing that allows for different combinations of the functional elements of the system based on the demands of a given treatment. For example, the system 200 can allow a user to leave the aspiration catheter in place for continued drainage after an initial treatment procedure. The modular cartridge housings can take a variety of forms. The illustrated embodiment shows a flattened rounded rectangular shape, but other shapes such as cylindrical designs can be used instead or in addition.

In the extended drainage scenario, once the initial infusion of thrombolytic and TRA ultrasound dispersal is completed, or at any other desired time, the infusion catheter 204 can be completely removed, and the proximal end of the aspiration catheter 202 capped, e.g., using the cap 262, so that the aspiration catheter can remain in place. When capped, the proximal end can be more compact than the full catheter system, further facilitating extended implantation. Additionally, the central bore of the aspiration catheter 202 can provide an additional drainage path in this configuration.

The system 200 can include removable hand and/or stereotactic controls, which can further facilitate extended implantation. Packaging the controls on a removable module can allow the modular "cartridge" to be as compact as possible, and can also allow the various catheter functions (e.g., steerability and infusion catheter advance/retract) to be locked when the controls are removed. This can prevent accidental actuation of any of these functions during extended implantation.

Figure 5B:
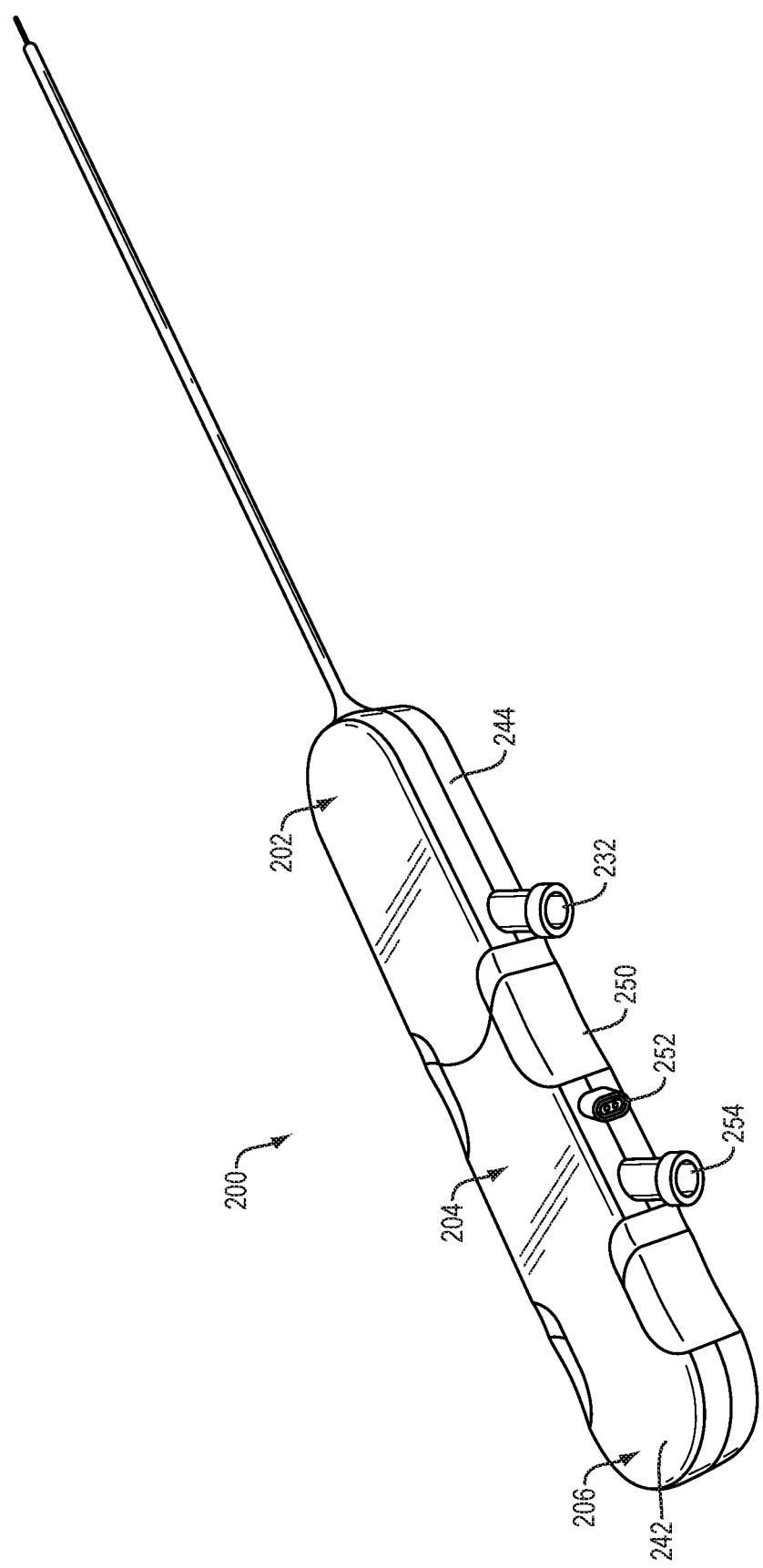
FIG. 5B is a perspective view of the system of FIG. 5A in a first assembly arrangement.

FIG. 5B illustrates a first arrangement of the system 200, in which the stylet 206 is inserted through the infusion catheter 204, which is inserted through the aspiration catheter 202. A proximal stylet cap or housing 242 can be positioned adjacent to a proximal infusion catheter housing 250 which can be positioned adjacent to a proximal aspiration catheter housing 244. The housings 242, 250, 244 can be modular cartridges that can be selectively mated to one another, e.g., via a snap-fit or other connection. The aspiration catheter housing 244 can include an aspiration port 232. The infusion catheter housing 250 can include an infusion port 254. The infusion catheter housing 250 can include a connector 252 for the TRA system 208. The arrangement of FIG. 5B can be used for initial placement of the system 200 within a patient.

Figure 5C:
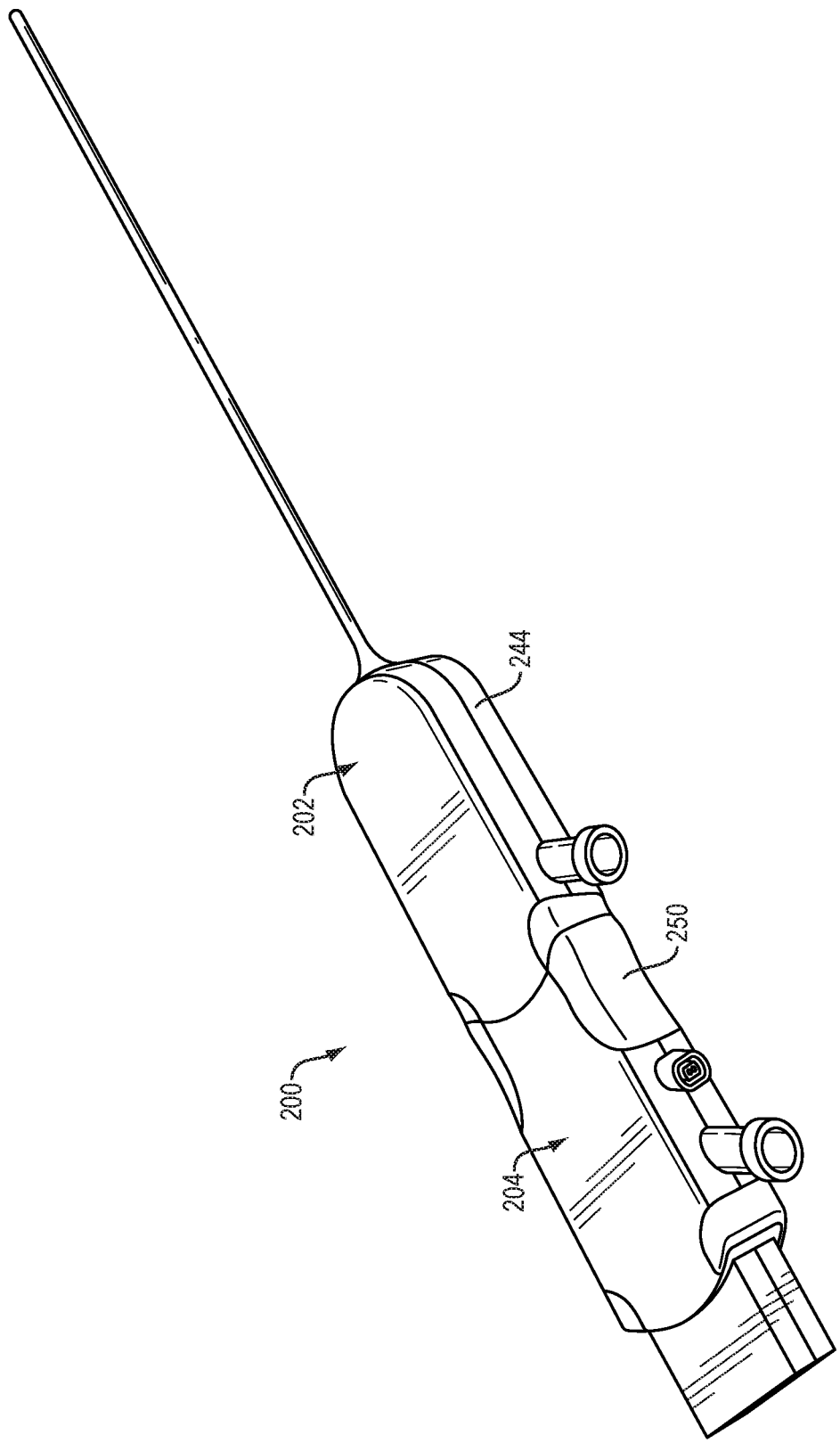
FIG. 5C is a perspective view of the system of FIG. 5A in a second assembly arrangement.

FIG. 5C illustrates a second arrangement of the system 200, which can be identical to the first arrangement except that the stylet 206 is removed. The stylet housing 242 can be replaced with the cap 262. The arrangement of FIG. 5C can be used for aspiration and/or infusion.

Figure 5D:
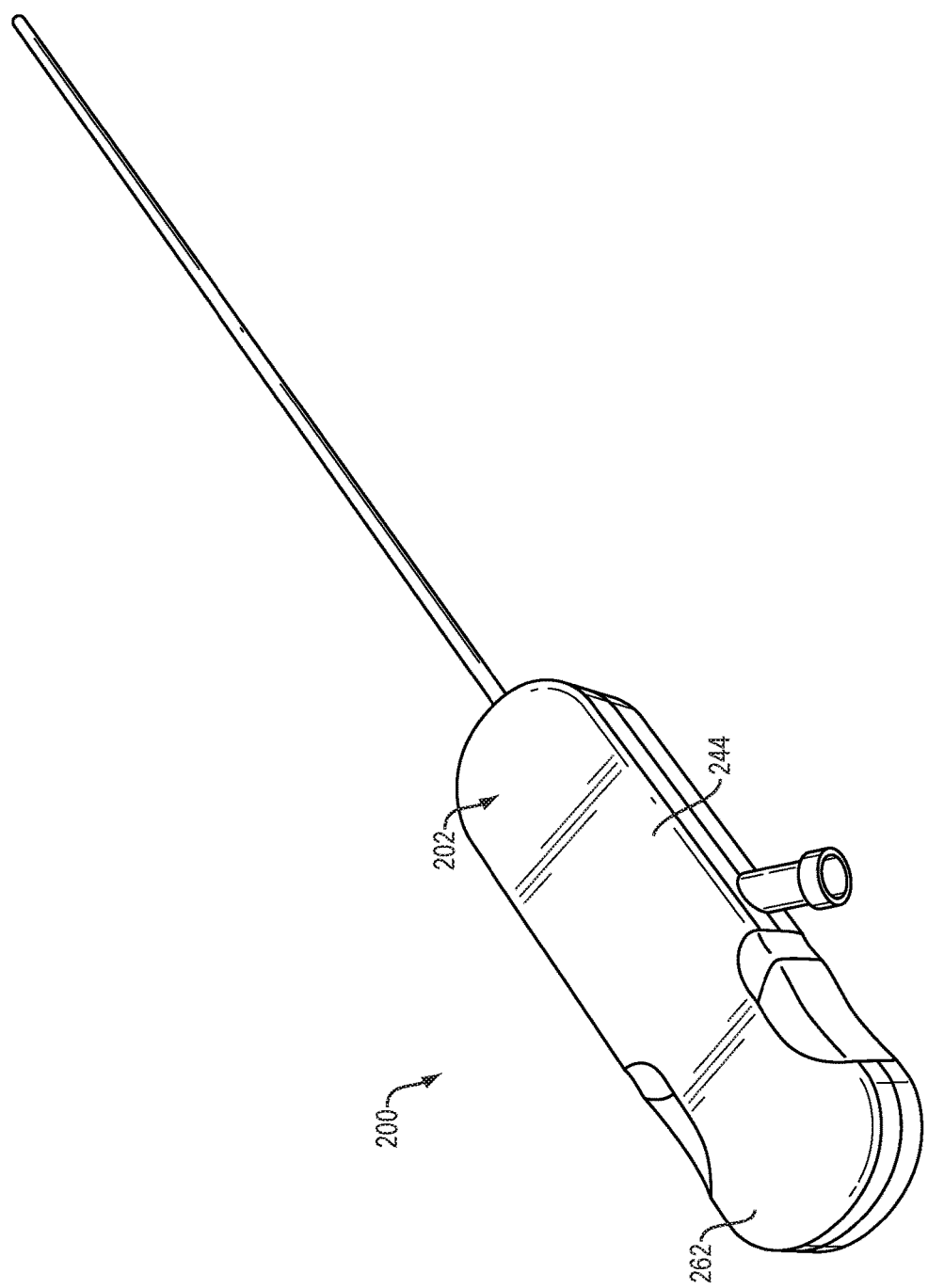
FIG. 5D is a perspective view of the system of FIG. 5A in a third assembly arrangement.

FIG. 5D illustrates a third arrangement of the system 200, which can be identical to the second arrangement except that the infusion catheter 204 is removed. The infusion catheter housing 250 can be replaced with the cap 262. The arrangement of FIG. 5D can be used for aspiration, e.g., as a compact drain assembly for long-term drainage. This arrangement can also be used for infusion, e.g., by infusing fluid through the aspiration lumen of the aspiration catheter 202.

Figure 5E:
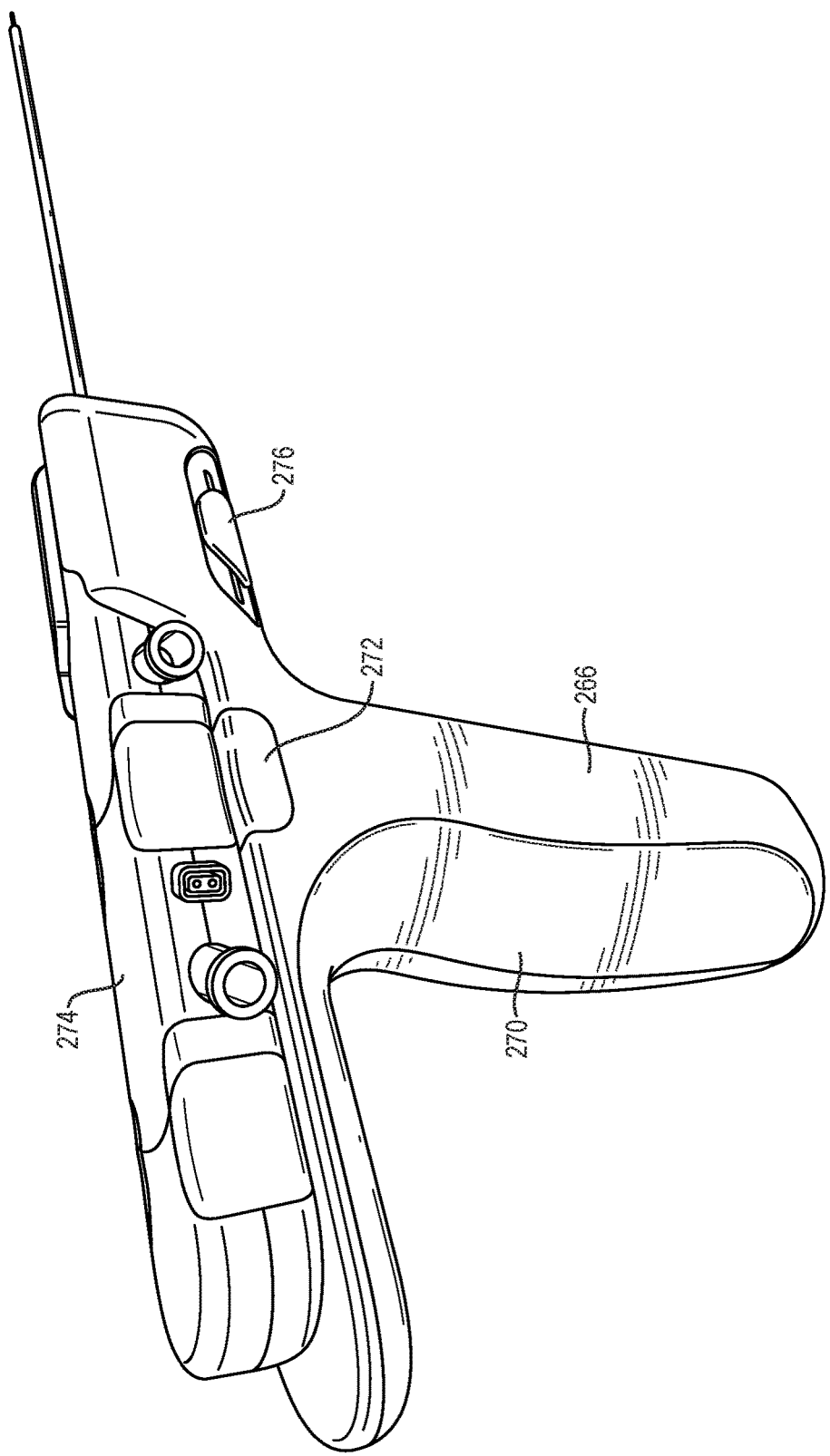
FIG. 5E is a perspective view of a catheter assembly and hand control module of the system of FIG. 5A.

FIG. 5E illustrates the system 200 in a configuration in which the modular cartridges of the catheter assembly (e.g., one or more of the stylet 206, the infusion catheter 204, and the aspiration catheter 202) are coupled to a hand control module 266. The hand control module 266 can provide single-handed, ambidextrous operation of the system controls, providing for efficient hand-guided procedures. The hand control module 266 can include an ergonomic handle 270, e.g., a pistol-grip handle, a pencil-type handle, etc. The hand control module 266 can include a release button 272 that can be actuated to release the catheter assembly 274 from the hand control module 266. The hand control module 266 can include one or more controls 276 for controlling operation of the catheter assembly 274. For example, the hand control module 266 can include sliding levers, rotating knobs, pushable buttons, or other control features for advancing or retracting the infusion catheter 204 relative to the aspiration catheter 202, or for steering one or both of the catheters 202, 204. The controls 276 can operate in a manner similar to that of the knobs 134A, 134B described above.

Figure 5F:
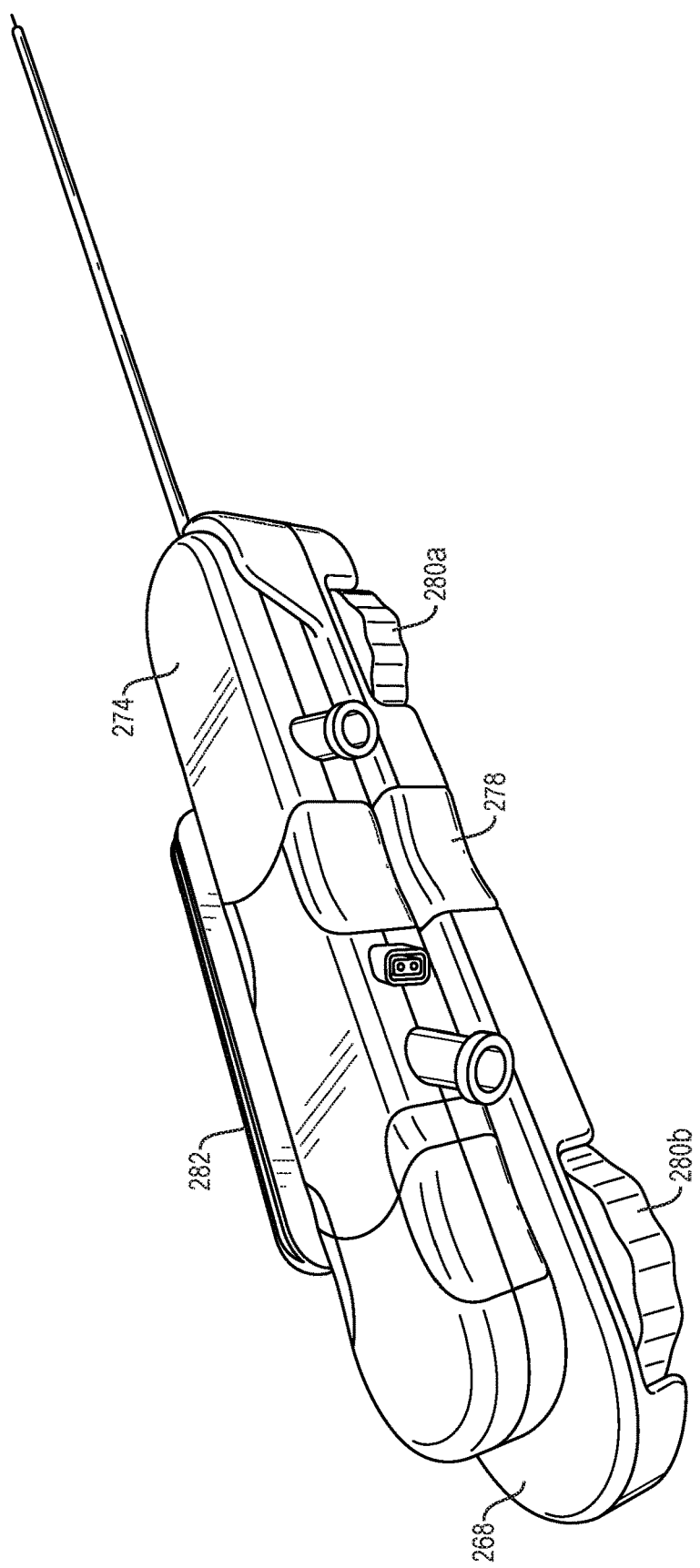
FIG. 5F is a perspective view of a catheter assembly and stereotactic module of the system of FIG. 5A.

FIG. 5F illustrates the system 200 in a configuration in which the modular cartridges of the catheter assembly (e.g., one or more of the stylet 206, the infusion catheter 204, and the aspiration catheter 202) are coupled to a low-profile stereotactic module 268. The stereotactic module 268 can provide controls in a compact platform for integration into stereotactic navigation systems. The stereotactic module 268 can include a release button 278 that can be actuated to release the catheter assembly 274 from the stereotactic module 268. The stereotactic module 268 can include one or more controls 280 for controlling operation of the catheter assembly 274. For example, the stereotactic module 268 can include sliding levers, rotating knobs, pushable buttons, or other control features for advancing or retracting the infusion catheter 204 relative to the aspiration catheter 202, or for steering one or both of the catheters 202, 204. The controls 280 can operate in a manner similar to that of the knobs 134A, 134B described above. In the illustrated embodiment, the stereotactic module 268 includes a forward control knob 280A for steering the aspiration catheter 202 and a rearward control knob 280B for advancing or retracting the infusion catheter 204 relative to the aspiration catheter 202. The stereotactic module 268 can include an attachment feature configured to attach the system 200 to a stereotactic frame or guidance system. For example, as shown, the stereotactic module 268 can include a dovetail mounting block 282 for integration into a stereotactic system.

FIGS. 6A-6E illustrate an exemplary method of using a catheter system, e.g., the system 100 or the system 200 disclosed herein, to treat a hematoma, such as a subdural hematoma.

Figure 6A:
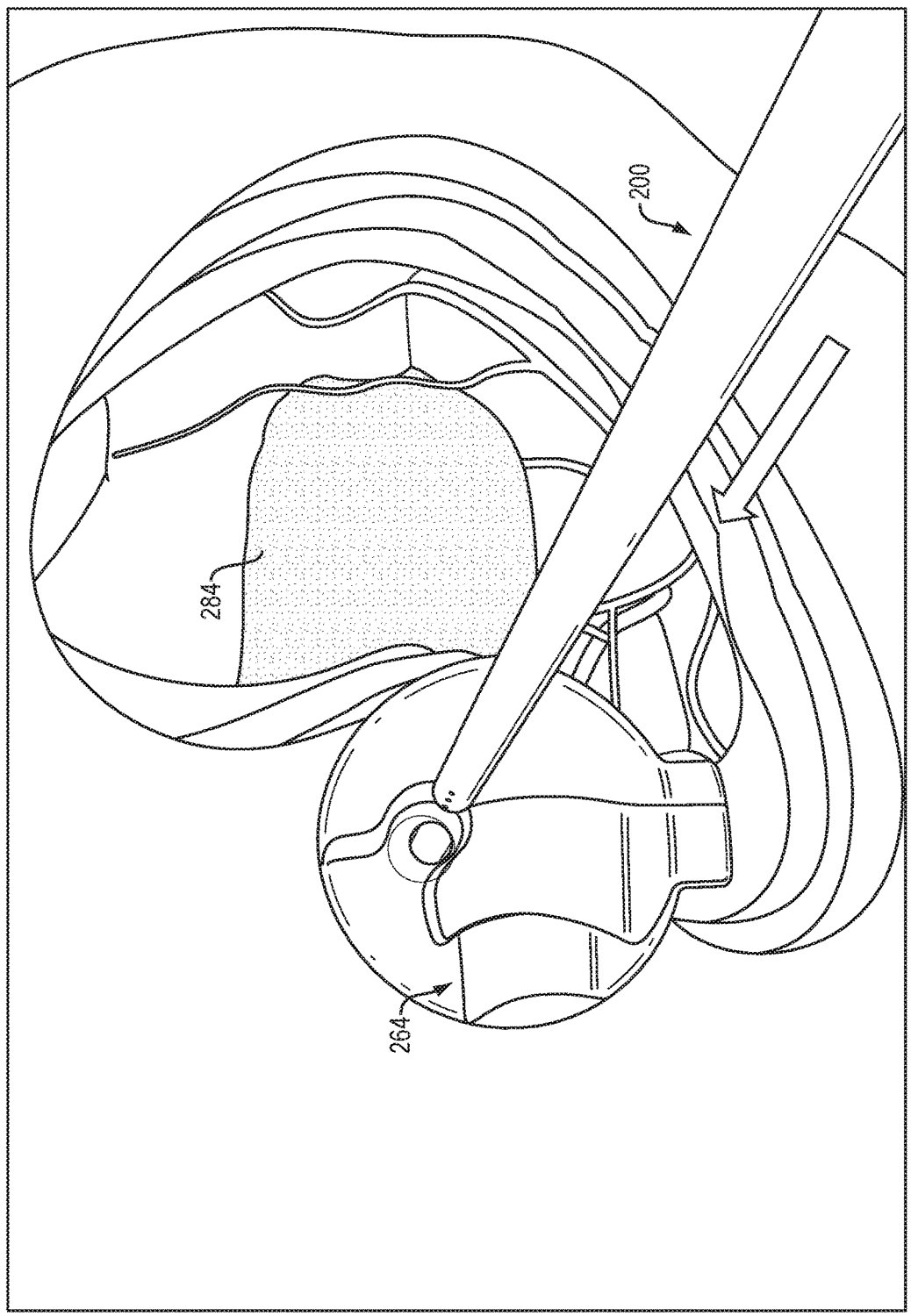
FIG. 6A is a schematic view of the system of FIG. 5A being used to treat a patient with a hematoma.

As shown in FIG. 6A, the site of the hematoma 284 can be accessed, for example by performing a twist drill craniostomy over the hematoma location. A skull anchor 264 can be installed and the catheter system 200 can be fed through the skull anchor into the subdural space.

Figure 6B:
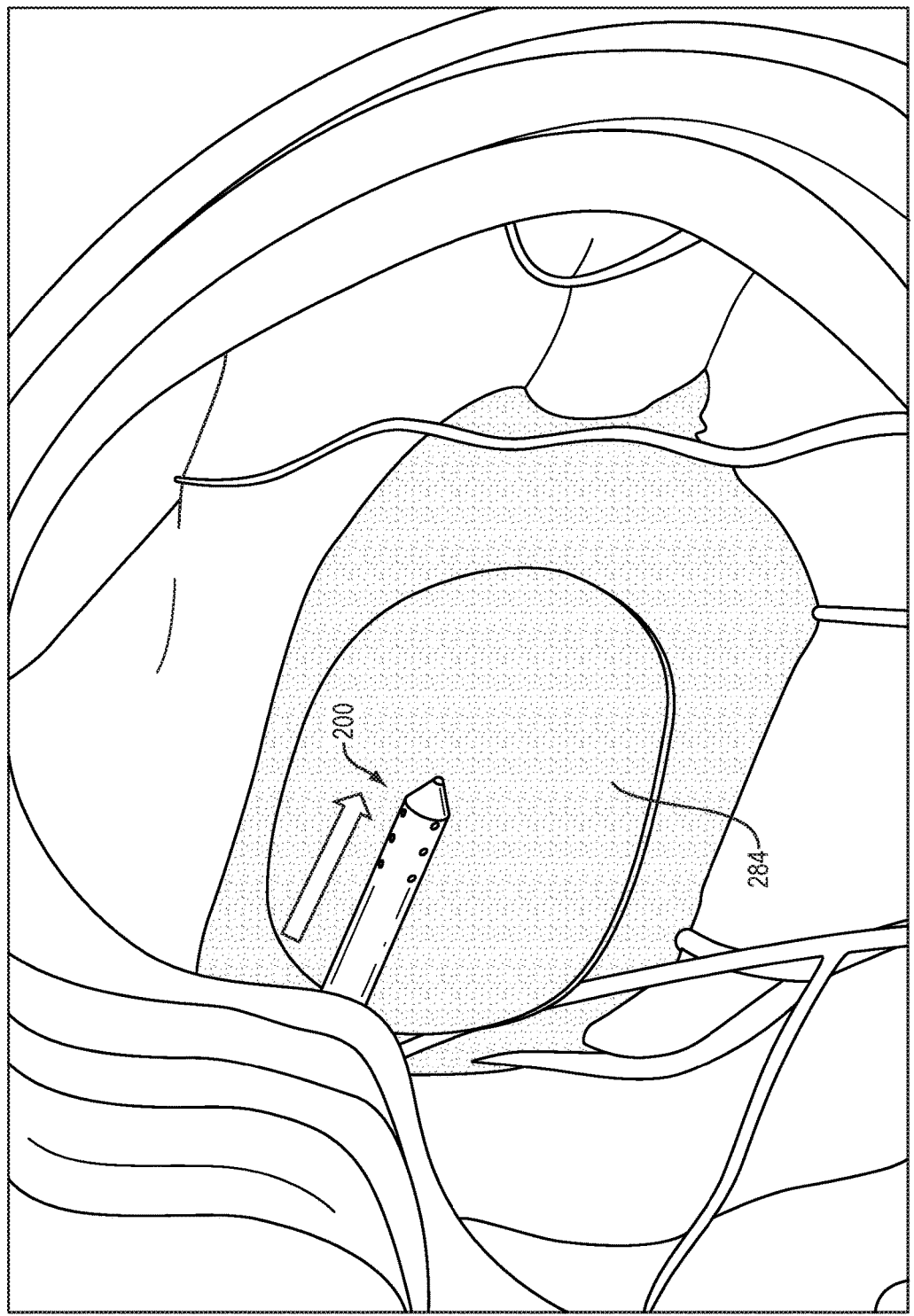
FIG. 6B is a schematic view of the hematoma of FIG. 6A with the catheter system of FIG. 5A inserted into the hematoma.

Steering functionality can be used to guide the distal end of the catheter system 200 into position within the hematoma 284, as shown in FIG. 6B.

As shown in FIG. 6C, the infusion/irrigation catheter 204 can be extended distally from the aspiration catheter 202 and into the hematoma 284. Irrigation and/or infusion of a thrombolytic or other drug 286 can be performed through the catheter 204.

Figure 6D:
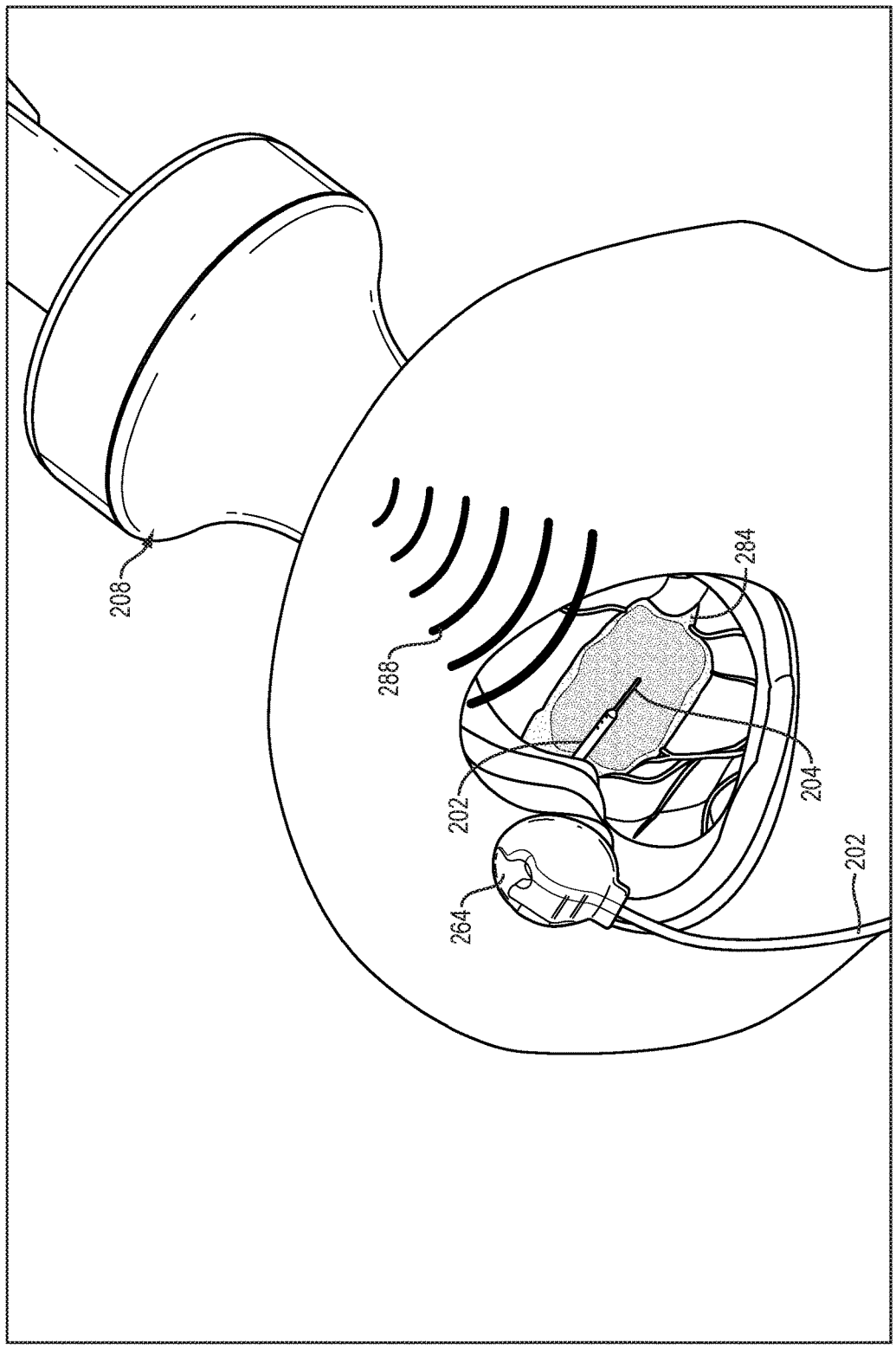
FIG. 6D is a schematic view of the hematoma of FIG. 6A with the catheter system of FIG. 5A applying ultrasound energy to the hematoma.

Focused ultrasound 288 can be applied to the hematoma 284 as shown in FIG. 6D, e.g., using a TRA system 208, to diffuse irrigation fluid and/or a drug and to break up the hematoma.

Figure 6E:
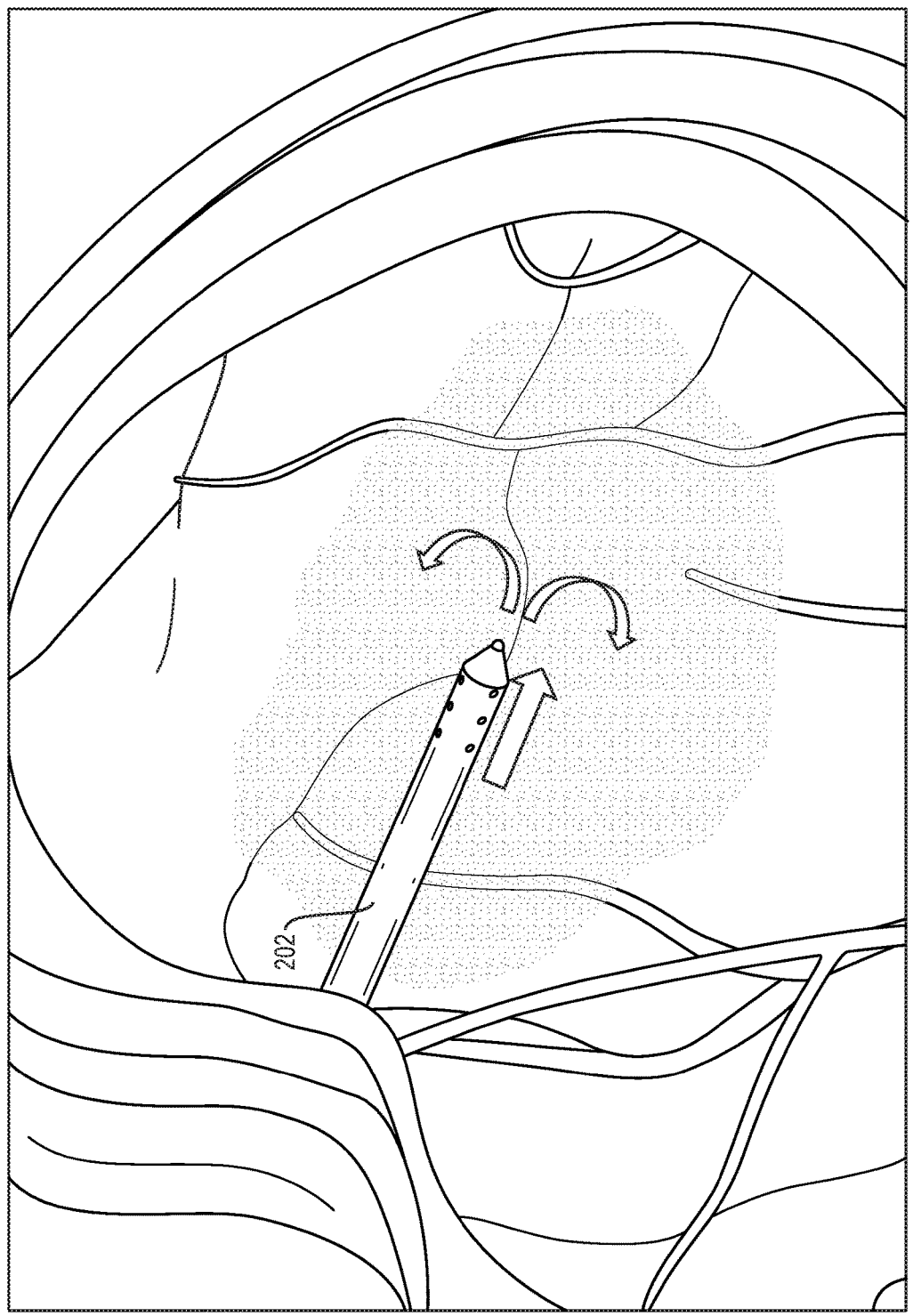
FIG. 6E is a schematic view of the hematoma of FIG. 6A being aspirated through the catheter system of FIG. 5A.

As shown in FIG. 6E, the infusion catheter 204 can be retracted and/or the aspiration catheter 202 can be advanced to aspirate the hematoma. Steering functionality can be used to target areas in need of aspiration.

While use in procedures to remove clots from the brain for treatment of stroke is generally contemplated herein, it will be appreciated that the methods and devices herein can be used for any of a variety of other medical or non-medical procedures. For example, the methods and devices herein can be used to dissolve and/or remove any type of tissue from any location within a human or animal patient, and can be used to treat various conditions other than stroke.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

Although the invention has been described by reference to specific embodiments, it should be understood that numerous changes may be made within the spirit and scope of the inventive concepts described. Accordingly, it is intended that the invention not be limited to the described embodiments.

The invention claimed is:

1. A method of treating a patient, comprising:
advancing a catheter system to a treatment site within the patient, wherein the catheter system comprises an infusion catheter slidably disposed within an aspiration catheter;
delivering at least one of a drug and an irrigation fluid to the treatment site through an infusion lumen of the infusion catheter of the catheter system;
advancing the aspiration catheter of the catheter system distally over the infusion catheter towards the treatment site after delivering the at least one of the drug and the irrigation fluid through the infusion catheter, the aspiration catheter being advanced distally over the infusion catheter such that a distal portion of the aspiration catheter is positioned at a distal portion of the infusion catheter; and
aspirating any material from the treatment site through an aspiration lumen of the aspiration catheter after advancing the aspiration catheter distally over the infusion catheter.

2. The method of claim 1, wherein the treatment site comprises a clot in a brain of the patient.

3. The method of claim 1, wherein the drug comprises a thrombolytic.

4. The method of claim 1, wherein the aspirated material comprises clot material.

5. The method of claim 1, wherein aspirating the material comprises steering the aspiration catheter within the treatment site.

6. The method of claim 1, wherein delivering the drug comprises enhancing diffusion rate of the drug by applying acoustic energy to the treatment site.

7. The method of claim 1, wherein delivering the drug comprises controlling the direction in which the drug is distributed using acoustic energy.

8. The method of claim 6, wherein the acoustic energy is emitted from a time reversal acoustic (TRA) system, wherein the TRA system comprises a hydrophone or microphone disposed in a distal end of the infusion catheter, one or more leads extending from the hydrophone or microphone to a proximal end of the infusion catheter, and a reverberator configured to time-reverse a signal detected by the hydrophone or microphone and emit acoustic waves based on the time-reversed signal.

9. The method of claim 1, wherein the infusion catheter has at least one outlet port for delivering at least one of the drug and the irrigation fluid to the treatment site and the aspiration catheter has at least one aspiration port for aspirating the material from the treatment site.

10. A method of treating a patient, comprising:
advancing a catheter system to a treatment site within the patient, wherein the catheter system comprises an infusion catheter slidably disposed within an aspiration catheter, wherein the infusion catheter includes at least one outlet port disposed in a lateral sidewall of a distal portion of the infusion catheter and adapted to deliver at least one of a drug and an irrigation fluid to the treatment site, and wherein the aspiration catheter is at least initially disposed relative to the infusion catheter such that the at least one outlet port is exposed for such delivery;
delivering at least one of the drug and the irrigation fluid to the treatment site through the at least one outlet port of the infusion catheter of the catheter system;
advancing the aspiration catheter of the catheter system distally over the infusion catheter towards the treatment site after delivering the at least one of the drug and the irrigation fluid through the infusion catheter, the aspiration catheter being advanced distally over the infusion catheter to cover the at least one outlet port of the infusion catheter; and
aspirating any material from the treatment site through an aspiration lumen of the aspiration catheter after advancing the aspiration catheter distally over the infusion catheter.

11. The method of claim 10, wherein the treatment site comprises a clot in a brain of the patient.

12. The method of claim 10, wherein the drug comprises a thrombolytic.

13. The method of claim 10, wherein the aspirated material comprises clot material.

14. The method of claim 10, wherein aspirating the material comprises steering the aspiration catheter within the treatment site.

15. The method of claim 10, wherein delivering the drug comprises enhancing diffusion rate of the drug by applying acoustic energy to the treatment site.

16. The method of claim 10, wherein delivering the drug comprises controlling the direction in which the drug is distributed using acoustic energy.

17. The method of claim 16, wherein the acoustic energy is emitted from a time reversal acoustic (TRA) system, wherein the TRA system comprises a hydrophone or microphone disposed in a distal end of the infusion catheter, one or more leads extending from the hydrophone or microphone to a proximal end of the infusion catheter, and a reverberator configured to time-reverse a signal detected by the hydrophone or microphone and emit acoustic waves based on the time-reversed signal.

18. The method of claim 10, wherein the aspiration catheter has at least one aspiration port for aspirating the material from the treatment site.

\* \* \* \* \*